(12) United States Patent
Gluschankof et al.

(10) Patent No.: US 9,493,769 B2
(45) Date of Patent: *Nov. 15, 2016

(54) YEAST-BASED ASSAY FOR MEASURING THE FUNCTIONAL ACTIVITY OF AN HIV-1 PROTEASE IN RESPONSE TO AN ANTIVIRAL AGENT

(75) Inventors: Pablo Gluschankof, Marseilles (FR); Didier Raoult, Marseilles (FR); Najoua Ben M'Barek, Marseilles (FR); Gilles Audoly, Marseilles (FR); Christelle Perrin-East, Marseilles (FR)

(73) Assignees: UNIVERSITE D'AIX-MARSEILLE, Marseilles (FR), part interest; CENTRE NATIONAL DE LA RECHERCHE SCIENTIFIQUE—CNRS, Paris (FR), part interest (*) Notice: Subject to any disclaimer, the term of this patent is extended or adjusted under 35 U.S.C. 154(b) by 736 days.

This patent is subject to a terminal disclaimer.

(21) Appl. No.: 12/504,456

(22) Filed: Jul. 16, 2009

(65) Prior Publication Data

US 2010/0028891 A1 Feb. 4, 2010

Related U.S. Application Data

(63) Continuation-in-part of application No. 12/503,174, filed on Jul. 15, 2009, now abandoned, which is a continuation-in-part of application No. 11/628,120, filed as application No. PCT/FR2005/001356 on Jun. 2, 2005, now Pat. No. 7,989,161.

(30) Foreign Application Priority Data

Jun. 2, 2004 (FR) ..................................... 04 05945

(51) Int. Cl.
 *G01N 33/569* (2006.01)
 *C12Q 1/37* (2006.01)
 (Continued)

(52) U.S. Cl.
 CPC ....... *C12N 15/1079* (2013.01); *C12N 15/1075* (2013.01); *C12Q 1/703* (2013.01); *C12N 2740/16222* (2013.01)

(58) Field of Classification Search
 CPC .......... C12N 15/1079; C12N 15/1075; C12N 2740/16222; C12Q 1/703
 See application file for complete search history.

(56) References Cited

U.S. PATENT DOCUMENTS

2002/0064838 A1* 5/2002 Parkin et al. ................ 435/91.4

FOREIGN PATENT DOCUMENTS

FR 2 729 973 8/1996

OTHER PUBLICATIONS

Blanco, R., et al., 2003, Cell killing by HIV-1 protease, J. Biol. Chem. 278(2):1086-1093.*

(Continued)

*Primary Examiner* — Jeffrey Parkin
(74) *Attorney, Agent, or Firm* — Young & Thompson

(57) ABSTRACT

A method of determining sensitivity or resistance of isolates of HIV retroviruses to a molecule includes a) amplifying sequences coding for a protease of a retrovirus to be studied, with or without the or some of amino acid sequences situated upstream and downstream of a cleavage site of a precursor in which the amino acid sequences are situated, b) recombining fragments of DNA, a final product of the amplification, and an expression vector allowing expression of sequence coding for the protease of the retrovirus to be studied under control of a known inducible promoter through co-transformation of the vector and the DNA fragments with at least one yeast cell, c) culturing co-transformed yeast cell or cells to obtain a sufficient number of transformants to perform a sensitivity or resistance test, and recovering transformants issuing from the co-transformed cell, on any suitable medium, d) incubating the transformants in the presence of a molecule to be tested, e) qualitatively or quantitatively analyzing the living cells, and f) deducing the sensitivity or resistance phenotype.

13 Claims, 5 Drawing Sheets

(51) Int. Cl.
C12N 15/10 (2006.01)
C12Q 1/70 (2006.01)

(56) References Cited

OTHER PUBLICATIONS

Liu, H., et al., 1992, Construction of a GAL1-regulated yeast cDNA expression library and its application to the identification of genes whose overexpression causes lethality in yeast, Genetics 132:665-673.*
Balmelli-Gallacchi, P., et al., 1999, A yeast-based bioassay for the determination of functional and non-functional estrogen receptors, Nuc. Acids Res. 27(8):1875-1881.*
Louis, J. M., et al., 1999, Autoprocessing of HIV-1 protease is tightly coupled to protein folding, Nat. Struct. Biol. 6(9):868-875.*
de Oliveira, T., et al., 2003, Variability at human immunodeficiency virus type 1 subtype C protease cleavage sites: an indication of viral fitness?, J. Virol. 77(17):9422-9430.*
Louis, J. M., et al., 1994, Kinetics and mechanism of autoprocessing of human immunodeficiency virus type 1 protease from an analog of the Gag-Pol polyprotein, Proc. Natl. Acad. Sci. USA 91:7970-7974.*
Wan, M., et al., 1996, Autoprocessing: an essential step for the activation of HIV-1 protease, Biochem. J. 316:569-573.*
Blanco Raquel et al., "Cell Killing by HIV-1 Protease," J. of Biol. Chem., vol. 278, Issue 2, Jan. 10, 2003, pp. 1086-1093 (Abstract only).
Liu Haoping et al., "Construction of a GAL1-Regulated Yeast cDNA Expression Library and Its Application to the Identification of Genes Whose Overexpression Causes Lethality in Yeast," Genetics Society of America, vol. 132, No. 3, 1992, pp. 665-673.
Angel Barco et al., "Poliovirus 2A-Pro-Expression Inhibits Growth of Yeast Cells," FEBS Letters, vol. 371, 1995, pp. 4-8.
M.G. Murray et al., "Inactivation of a Yeast Transactivator by the Fused HIV-1 Proteinase: a Simple Assay for Inhibitors of the Viral Enzyme Activity," Gene, Elsevier Biomedical Press, Amsterdam, NL, vol. 134, No. 1, 1993, pp. 123-128 (Abstract only).
G. Adjorlolo-Johnson et al., "Prospective Comparison of Mother-to-Child Transmission of HIV-1 and HIV-2 in Abidjan, Ivory Coast," JAMA, Aug. 10, 1994, vol. 272, No. 6, pp. 462-466.
R. Ancelle et al., "Long Incubation Period for HIV-2 Infection," The Lancet, Mar. 21, 1987, pp. 688-689.
S. Andersson et al., "Plasma Viral Load in HIV-1 and HIV-2 Singly and Dually Infected Individuals in Guinea-Bissau, West Africa: Significantly Lower Plasma Virus Set Point in HIV-2 Infection Than in HIV-1 Infection," Arch. Intern. Med., Nov. 27, 2000, vol. 160, pp. 3286-3293.
P. Boross et al., "Effect of Substrate Residues on the P2' Preference of Retroviral Proteinases," Eur. J. Biochem., 1999, vol. 264, pp. 921-929.
J. Büttner et al., "Screening of Inhibitors of HIV-1 Protease Using an *Escherichia coli* Cell Assay," Biochemical and Biophysical Research Communications, 1997, vol. 233, No. 1, pp. 36-38.
F. Clavel et al., "Isolation of a New Human Retrovirus from West African Patients with AIDS," Science, Jul. 18, 1986, vol. 233, pp. 343-346.
F. Clavel et al., "Molecular Cloning and Polymorphism of the Human Immune Deficiency Virus Type 2," Nature, Dec. 1986, vol. 324, pp. 691-695.
C.L. Langley et al., "HIV-1, HIV-2, Human Papillomavirus Infection and Cervical Neoplasia in High-Risk African Women," AIDS, 1996, vol. 10, No. 4, pp. 413-417.
R. Marlink et al., "Reduced Rate of Diasease Development After HIV-2 Infection as Compared to HIV-1," Science, Sep. 9, 1994, vol. 265, No. 5178, pp. 1587-1590.
R. Marlink, "Lessons from the Second AIDS Virus, HIV-2," AIDS, 1996, vol. 10, pp. 689-699.
M.D. Moody et al., "A Side Chain at Position 48 of the Human Immunodeficiency Virus Type-1 Protease Flap Provides an Additional Specificity Determinant," Virology, 1995, vol. 207, pp. 475-485.
S. Oroszlan et al., "Retroviral Proteinases," Current Topics in Microbiology and Immunology, 1990, vol. 157, pp. 153-185.
F.J. Palella et al., "Declining Morbidity and Mortality among Patients with Advanced Human Immunodeficiency Virus Infection," The New England Journal of Medicine, Mar. 26, 1998, vol. 338, No. 13, pp. 853-860.
S.C. Pettit et al., "Analysis of Retroviral Protease Cleavage Sites Reveals Two Types of Cleavage Sites and the Structural Requirements of the P1 Amino Acid," The Journal of Biological Chemistry, Aug. 5, 1991, vol. 266, No. 22, pp. 14539-14547.
S.C. Pettit et al., "The p2 Domain of Human Immunodeficiency Virus Type 1 Gag Regulates Sequential Proteolytic Processing and Is Required to Produce Fully Infectious Virions," Journal of Virology, Dec. 1994, vol. 68, No. 22, pp. 8017-8027.
S.J. Popper et al., "Lower Human Immunodeficiency Virus (HIV) Type 2 Viral Load Reflects the Difference in Pathogenicity of HIV-1 and HIV-2," The Journal of Infectious Diseases, Oct. 1999, vol. 180, pp. 1116-1121.
A-G. Poulsen et al., "Prevalence of and Mortality from Human Immunodeficiency Virus Type 2 in Bissau, West Africa," The Lancet, Apr. 15, 1989, pp. 827-830.
V. Soriano et al., "Human Immunodeficiency Virus Type 2 (HIV-2) in Portugal: Clinical Spectrum, Circulating Subtypes, Virus Isolation, and Plasma Viral Load," Journal of Medical Virology, 2000, vol. 61, pp. 111-116.
E. Vittinghoff et al., "Combination Antriretroviral Therapy and Recent Declines in AIDS Incidence and Mortality," The Journal of Infectious Diseases, 1999, vol. 179, pp. 717-720.
A. Wilkins et al., "The Epidemiology of HIV Infection in a Rural Area of Guinea-Bissau," AIDS, 1993, vol. 7, No. 8, pp. 1119-1122.

* cited by examiner

YEAST-BASED ASSAY FOR MEASURING THE FUNCTIONAL ACTIVITY OF AN HIV-1 PROTEASE IN RESPONSE TO AN ANTIVIRAL AGENT

RELATED APPLICATIONS

This is a continuation-in-part of U.S. application Ser. No. 12/503,174, filed Jul. 15, 2009, which is a continuation-in-part of U.S. application Ser. No. 11/628,120, filed Dec. 1, 2006, which is a §371 of International Application No. PCT/FR2005/001356, with an international filing date of Jun. 2, 2005 (WO 2006/000693 A1, published Jan. 5, 2006), which is based on French Patent Application No. 04/05945, filed Jun. 2, 2004.

TECHNICAL FIELD

This disclosure relates to methods for determining the sensitivity or resistance of retroviruses isolates to molecules, therapeutic retroviral treatments based on viral protease inhibitors, and diagnostic kits derived from the implementation of the methods.

BACKGROUND

The etiological agents of AIDS are the human immunodeficiency viruses types 1 and 2. These viruses, which share certain clinical and biological characteristics, have major differences, in particular with regard to the ways in which the host is infected. Thus, infection by HIV-2 is more difficult than by HIV-1 (Ancelle R, O Bletry, A C Baglin, F Brun-Vezinet, M A Rey and P Godeau, 1987, Long incubation period for HIV-2 infection. Lancet. 1:688-9; Marlink R, P Kandki, I Thior, K Travers, G Eisen, T Siby, I Traore, C C Hsieh, M C Dia and E H Gueye. 1994. Reduced rate of disease development after HIV-2 infection as compared to HIV-1. Science. 265:1587-90; Adjorlolo-Johnson G, K M De Cock, E Ekpini, K M Vetter, T Sibailly, K Brattegaard, D Yavo, R Doorly, J P Whitaker and L Kestens. 1994. Prospective comparison of mother-to-child transmission of HIV-1 and HIV-2 in Abidjan, Ivory Coast. JAMA. 272:462-6; Marlink, R. 1996. Lessons from the second AIDS virus, HIV-2. AIDS. 10:689-99.), the plasma viral load of individuals infected by HIV-2 is less high and/or lower than that in individuals infected by HIV-1 (Andersson S, H Norrgren, Z da Silva, A Biague, S Bamba, S Kwok, C Christopherson, G Biberfeld, and J Albert. 2000. Plasma viral load in HIV-1 and HIV-2 singly and dually infected individuals in Guinea-Bissau, West Africa: significantly lower plasma virus set point in HIV-2 infection than in HIV-1 infection. Arch. Intern. Med. 160:3286-93; Popper S J, A D Sarr, K U Travers, A Gueye-Ndiaye, S Mboup, M E Essex, and P J Kanki. 1999. Lower human immunodeficiency virus (HIV) type 2 viral load reflects the difference in pathogenicity of HIV-1 and HIV-2. J Infect Dis. 180:1116-21.), and the individuals infected by HIV-2 develop the illness more slowly (Vittinghoff E, S Scheer, P O'Malley, G Colfax, S D Holmberg and S P Buchbinder. 1999. Combination antiretroviral therapy and recent declines in AIDS incidence and mortality. J Infect Dis. 179:717-20; Blanco R, Carrasco, L, and Ventoso, I. 2003. Cell killing by HIV-1 protease. J. Biol. Chem. 278:1086-93; Liu H, Krizek J, and Bretscher A. 1992. Construction of a GAL1-regulated yeast cDNA expression library and its application to the identification of genes whose overexpression causes lethality in yeast. Genetics 132:665-673).

HIV-2 was identified for the first time in West Africa in 1986 (Clavel F, D Guetard, F Brun-Vezinet, S Chamaret, M A Rey, M 0 Santos-Ferreira, A G Laurent, C Dauguet, C Katlama, and C Rouzioux. 1986. Isolation of a new human retrovirus from West African patients with AIDS. Science. 233:343-6). In this region, the prevalence of HIV-2 varies between 1% and 10% (Langley C L, E Benga-De, C W Critchlow, I Ndoye, M D Mbengue-Ly, J Kuypers, G Woto-Gaye, S Mboup, C Bergeron, K K Holmes, and N B Kiviat. 1996. HIV-1, HIV-2, human papillomavirus infection and cervical neoplasia in high-risk African women. AIDS. 10:413-7; Poulsen A G, B Kvinesdal, P Aaby, K Molbak, K Frederiksen, F Dias and E Lauritzen. 1989. Prevalence of and mortality from human immunodeficiency virus type 2 in Bissau, West Africa. Lancet. 1:827-31; Wilkins A, D Ricard, J Todd, H Whittle, F Dias, and A Paulo Da Silva 1993. The epidemiology of HIV infection in a rural area of Guinea-Bissau. AIDS. 7:1119-22). The majority of these cases of infection by HIV-2, outside West Africa, are found in European countries and especially in Portugal where the individuals infected by HIV-2 represent 13% of the population infected by human immunodeficiency viruses (Soriano V, P Gomes, W Heneine, A Holguin, M Doruana, R Antunes, K Mansinho, W M Switzer, C Araujo, V Shanmugam, H Lourenco, J Gonzalez-Lahoz and F Antunes. 2000. Human immunodeficiency virus type 2 (HIV-2) in Portugal: clinical spectrum, circulating subtypes, virus isolation, and plasma viral load. J. Med. Virol. 61:111-6). In France, it has been estimated that 1% of the population infected by HIV is infected by the type 2 virus.

In developed countries, the individuals infected by HIV-1 and/or by HIV-2 are treated by chemical therapy, composed of molecules having an inhibiting activity for one or other of the two viral enzymes: Reverse Transcriptase and Protease.

Moreover, the individuals infected by HIV-1 and/or by HIV-2 are also treated by chemical therapy, composed of molecules having an inhibiting activity for the viral entry process or for the viral enzymes: Reverse Transcriptase, Protease, and Integrase.

Although that treatment has significantly helped to reduce morbidity and mortality caused by HIV infection (Palella F J, Jr, K M Delaney, A C Moorman, M O Loveless, J Fuhrer, G A Satten, D J Aschman and S D Holmberg. 1998. Declining morbidity and mortality among patients with advanced human immunodeficiency virus infection. HIV Outpatient Study Investigators. N. Engl. J. Med. 338:853-60; Vittinghoff E, S Scheer, P O'Malley, G Colfax, S D Holmberg and S P Buchbinder. 1999. Combination antiretroviral therapy and recent declines in AIDs incidence and mortality. J. Infect. Dis. 179:717-20), some cases of therapeutic failure have been observed.

The possibility of amplifying, from the plasma, RNA or cell DNA of the individuals infected by HIV-1 and in therapeutic failure, has made it possible to understand at the molecular level the spontaneous or progressive inefficacy of therapeutic treatments. The determination, in particular, of the nucleic sequence of the two viral enzymes Reverse Transcriptase and Protease has shown the appearance of a certain number of mutations. The results obtained during studies in vitro in which a wild type viral strain (and therefore sensitive to treatments) carried the mutations have clearly demonstrated the implication of these mutations in the resistance of the virus to treatment.

Researchers have therefore done a certain amount of work on these mutations and the resistances that they generate to orient and guide the choice of therapeutic treatment and optimize its efficacy.

Two different technical approaches were developed to orient therapeutic treatments. One consisted of searching only the already known mutations within the nucleic acid sequences coding for the viral proteins and is called the genotyping approach. The other one, that does not need knowledge of the presence of resistant mutations within the viral sequences, consists of testing in a cell based system the inhibition of viral replication in the presence of inhibiting molecules, and is called the phenotyping approach.

Unfortunately, the economic strategies of the laboratories have the majority of the time led to a general lack of interest in the scientific community with regard to the treatment of patients infected by HIV-2 (the populations most affected by HIV-2 being mainly those in developing countries) or have led to unsuitable solutions: treatments, tests and analyses that are too expensive, diagnoses, for example, phenotyping diagnoses that are too lengthy or impossible to implement on site, absence of competent structures in the country concerned, etc.

Thus, the results obtained during the various studies carried out on HIV-2 have not been sufficiently consistent to make it possible to formulate a correlation between a particular mutation of the HIV-2 protease, and a resistance phenotype.

It should be noted that, the progression of the illness being slower in individuals infected by HIV-2 than in those infected by HIV-1, the counting of T CD4 cells and determination of the plasma viral load do not rapidly take account of the emergence of resistant strains in patients under treatment.

There exist at the present time several companies that provide the resistance profile of an HIV strain isolated from an infected patient through phenotyping. Conceptionally the three tests resemble each other and are based on the ability of each protease inhibitor to inhibit the release of an infectious recombinant virus comprising the protease of the virus infecting the patient. The companies are: EUROFINS-Viralliance (France), which produces Phenoscript™, Virco-Johnson & Johnson (Belgium-USA), which produces Antivirogram™, and Monogram Biosciences, ex Virologic (United States), which produces Phenosense™. In the three cases, performing those tests requires significant logistic organization, personnel skilled in molecular biology and virology, and expensive infrastructures of the P3 secure laboratory type (it would appear that a complete profile would currently cost between 800 and 1,000 euros per sample). The delay existing between the time when the biological material arrives at the laboratories and the time when the resistance profile is established varies, for each strain of HIV-1, between two and three weeks.

Under these circumstances, putting on the market a reliable rapid test, for example, a phenotyping test that is simple to implement and inexpensive has become imperative. Such a test would assist treating physicians to monitor the appearance of resistant strains in patients infected by retroviruses, in particular HIV 1 or 2, in particular for deprived populations. Moreover, this test could also be used for a "high speed" and/or "high throughput" research for new molecules having inhibiting activity for the retrovirus protease.

SUMMARY

We provide a method of determining sensitivity or resistance of isolates of HIV retroviruses to a molecule including a) amplifying sequences coding for a protease of a retrovirus to be studied, with or without the or some of amino acid sequences situated upstream and downstream of a cleavage site of a precursor in which the amino acid sequences are situated, b) recombining fragments of DNA, a final product of the amplification, and an expression vector allowing expression of sequence coding for the protease of the retrovirus to be studied under control of a known inducible promoter through co-transformation of the vector and the DNA fragments with at least one yeast cell, c) culturing co-transformed yeast cell or cells to obtain a sufficient number of transformants to perform a sensitivity or resistance test, and recovering transformants issuing from the co-transformed cell, on any suitable medium, d) incubating the transformants in the presence of a molecule to be tested, e) qualitatively or quantitatively analyzing the living cells, and f) deducing the sensitivity or resistance phenotype.

We also provide a diagnostic kit that performs the method, including nucleotide primers selected from the group consisting of SEQ ID NO 38, 39, 40, 41, 42, 48, 51, 52, 53, 54, 55, 56, 57 and 58; at least one expression vector; at least one strain of yeast; and at least one multi-well plate or other support.

DETAILED DESCRIPTION

Figure 1:
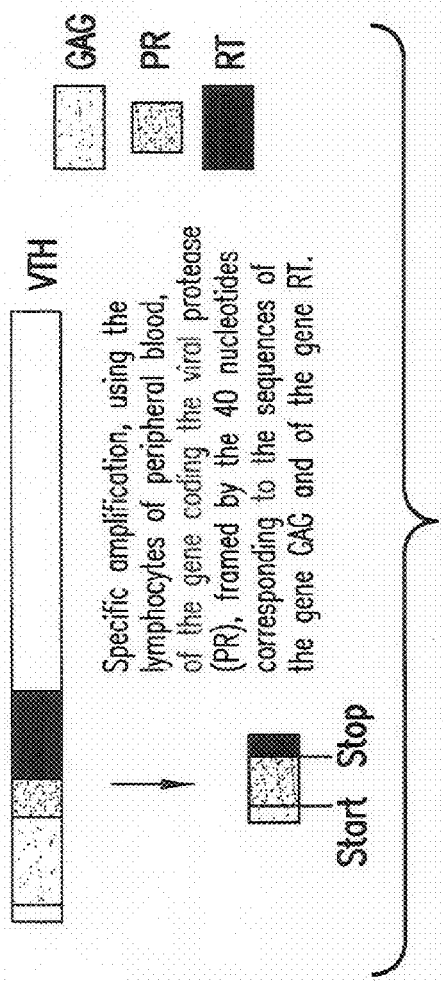
FIGS. 1 and 2 are schematic representations of the co-transformation of the pRS316-Gal1/10M vector cleaved by the Not1 restriction enzyme with the product of the second PCR to obtain a transformed yeast cell having the sequence of the HIV-2 protease under the control of the inducible promoter Gal1.

We provide methods for determining the sensitivity or resistance of retroviruses such as HIV to molecules, therapeutic treatments based on viral protease inhibitors, by the use of yeast. In other words, we provide for the use of yeast to determine the resistance or sensitivity of the viral protease to molecules, and/or the chemical molecules used in the context of therapeutic protocols. We also provide diagnostic kits comprising the elements necessary for implementing the method.

More particularly, the methods make it possible to determine, quickly and at low cost, the resistance phenotype of the HIV-2 protease in infected patients. The methods also make it possible to determine, quickly and at low cost, the resistance phenotype of HIV-1 protease in infected patients. The methods further allow the "high speed" and/or "high throughput" search for new chemical molecules having an inhibiting activity for the viral protease with a view to developing novel therapeutic treatments.

We thus provide means permitting the rapid and low-cost definition of the resistance phenotype of the HIV-2 or HIV-1 protease in infected patients, by virtue of the use of yeast. Our methods can also be implemented to define the resistance phenotype of the HIV-1 protease, or the protease of any other retrovirus.

The sequences coding some therapeutic targets, for example, reverse transcriptase protease, and integrase, as well as the so-called "structure proteins" (matrix, capsid, nucleocapsid), are situated within a common polypeptide precursor called Gag-Pol, coded by the gag-pol viral gene (Clavel F, Guyader M, Guetard D, Salle M, Montagnier L. Alizon M. 1986. Molecular cloning and polymorphism of the human immune deficiency virus type 2. Nature, 324: 691-5). It is the action of the viral protease that, by hydrolysis of specific peptide bonds referred to as cleavage sites, framing the primary sequences of the various constituents of the precursor, is responsible for the release of these proteins (Oroszlan S and Luftig RB. 1990. Retroviral proteinases. Curr Top Microbiol Immunol. 157:153-85). It has been shown that, for the HIV-1 protease, the amino acid sequences situated upstream and downstream of the cleavage site fulfill an important role in the recognition event of the enzyme for its substrate, and therefore are determinant for its proteolytic activity (Pettit S C, Simsic J, Loeb D D, Everitt L, Hutchison CA 3rd, Swanstrom R. 1991. Analysis of retroviral protease cleavage sites reveals two types of cleavage sits and the structural requirements of the P1 amino acid. J. Biol. Chem. 266:14539-47, Pettit S C, Moody M D, Wehbie R S, Kaplan A H, Nantermet P V, Klein C A, Swanstrom R. 1994). The p2 domain of human immunodeficiency virus type 1 Gag regulates sequential proteolytic processing and is required to produce fully infectious virions (J Virol. 68:8017-27, Moody M D, Pettit S C, Shao W, Everitt L, Loeb D D, Hutchison C A 3rd, Swanstrom R. 1995). A side chain at position 48 of the human immunodeficiency virus type-1 protease flap provides an additional specificity determinant (Virology. 207:475-85, Boross P, Bagossi P, Copeland T D, Oroszlan S, Louis J M, Tozser J. 1999. Effect of substrate residues on the P2' preference of retroviral proteinases. Eur J Biochem. 264:921-9).

A scientific article that appeared in 2003 demonstrated that the expression of the HIV-1 protease by the yeast *Saccharomyces cerevisiae* caused the death of the latter through a still unknown mechanism, the consequence of which was the cell lysis of the yeast in question (Blanco R, Carrasco L and Ventoso I. 2003. Cell killing by HIV-1 protease. J. Biol. Chem. 278:1086-93).

We demonstrated that the same phenomenon occurred when the yeasts expressed the HIV-2 protease. Consequently, by inhibiting viral enzymatic activity by modification of its catalytic site, we succeeded in preventing the appearance of this cell event.

In addition, Blanco et al (Blanco R, Carrasco L, and Ventoso I. 2003. Cell killing by HIV-1 protease. J. Biol. Chem. 278:1086-93) also showed that the inhibition of the HIV-1 protease by one of the inhibitors used in anti-HIV therapy inhibited cell death of the yeast caused by expression of the viral protease. Because of this fact, it is possible to quantitatively measure the sensitivity and resistance of the protease of infected individuals to the various inhibited molecules.

Moreover, we worked on the smallest active Gag-Pol precursor that, once expressed in yeast, induces cell death through protease activity. Since the definition of a functional protease precursor protein is the one from which the protease can, sequentially, be cleaved off and kill then the expressing yeast, we created and expressed a large number of truncated Gag-Pol precursors in yeast where the protease cleavage sit was either present or absent by specific nucleic acid mutation. We surprisingly found that the smallest active protease precursor was defined as the smallest Gag-Pol sequence, containing the protease flanked by its cleavage sits that only induces yeast cell death when the cleavage site situated at the N-terminal part of the protease sequence is present. In the absence of this one, the expressed precursor is unable to disturb cell growth.

We have surprisingly found that a sequence encoding for the protease preceded by the 6 amino acids of the cleavage sit and followed by at least one amino acid of the other cleavage site was the smallest active precursor form that induces cell death when expressed in yeast.

Our methods therefore make it possible to determine, in the cellular context of the yeast, the sensitivity phenotype of the viral protease of a retrovirus such as HIV-2 or HIV-1, to drugs with an inhibiting activity.

In other words, it makes it possible to determine the sensitivity or resistance of isolates of retroviruses such as HIV (human immunodeficiency virus) to chemical molecules having an inhibiting activity on the viral protease or to therapeutic treatments based on inhibitors of the viral protease, characterized by the use for this purpose of at least one yeast whose cell lysis is caused by expression of the retrovirus protease.

We surprisingly discovered that, not only the specific sequence coding for protease, but also a precursor sequence of HIV-1 protease when incorporated in an expression vector, through a co-transformation proceeding in yeast allows the expression of protease and cause the death of the yeast. In other words, we discovered that sequences comprising protease HIV-1 coding sequence extracted from for example, infected blood or cells are functionally expressed in yeast.

Therefore, our methods allow us to determine the sensitivity or resistance of retrovirus protease to molecules in a cell based non-infectious system in the presence of its natural substrate. Further, our methods allow us to test molecules having an effect on the activity of the protease and also on expression of the protease. Moreover, our methods allow us to test molecules having a direct effect on the activity of the protease toward its natural substrate that is, for example, the protease precursor. For example, the method allows us to test molecules inhibiting the activity of protease by acting on the sequence coding for the protease, and/or coding for the protease precursor, by acting on the translation of the protease, by acting on the transcription mechanism, and/or on the protease activity.

Moreover, our methods allow for the determination of the sensitivity or resistance of protease having at least one mutation, for example, in the protease and the protease precursor coding nucleic acids sequence.

Schematically, the methods comprise an expression vector, choice of the cell system, method of expressing proteases of infected individuals and test of susceptibility to drugs.

It comprises the following steps:
  optionally extracting the nucleic acids, DNA and/or RNA from body fluids or cells (blood or other) taken from an individual or animal infected by the retrovirus, by any suitable means;
  amplifying the sequences coding for the protease of the retrovirus to be studied;
  recombining the fragments of DNA, the final product of the amplification, and an expression vector allowing the expression of the sequence coding for the protease, and/or any form or length of the protease precursor of the retrovirus to be studied under the control of a known inducible promoter, through co-transformation of the vector and DNA fragments with at least one yeast cell whose cell lysis is caused by the expression of the retrovirus protease;
  culturing the co-transformed yeast cell or cells to obtain a sufficient number of transformants to perform the sensitivity or resistance test, and recovery of the transformants issuing from the co-transformed cell, on any suitable medium;

incubating the transformants in the presence of, preferably with an increasing concentration, of each molecule to be tested;

qualitatively or quantitatively analyzing the living cells; and deducing the resistance phenotype.

The nucleic acids may be extracted from cells infected by a retrovirus, and/or body fluids from an infected individual or animal, and/or blood from an infected individual or animal, and/or from infected culture cell media.

The molecules to be tested, also called "test molecules," are selected from the group comprising molecules of a library, chemical molecules, natural molecules and molecules extracted from plants.

The test molecules may be selected from the group comprising chemical molecules having an inhibiting activity on the viral protease, therapeutic treatments based on inhibitors of the viral protease or of the viral maturation.

The sequences of the protease amplified according to the method include those coding for the isolated protein or those coding for the protein and comprising all or some of the amino acid sequences situated upstream and downstream of the cleavage site of the protein precursor in which they are situated.

The retrovirus may be HIV-1.

The amplified sequences coding for the protease of the retrovirus to be studied according to the method can be mutated or non-mutated sequence. The amplified sequences coding for the protease of the retrovirus, for example, HIV-1, to be studied may be selected from the group comprising SEQ ID NO 10 to 37.

The yeast used in the method may be of the type of *Saccharomyces cerevisiae*.

The nucleic acids may be amplified, for example, by Polymerase Chain Reaction using couple of primers selected from the group comprising SEQ ID NO 38, 39, 40, 41, 42, 48, 51 to 58.

The protocols used in the laboratory with a view to obtaining yeast transformants coding for an exogenous gene generally begin with a first step for obtaining the fragments of DNA coding for the gene of interest, either by gene amplification (Polymerase Chain Reaction (PCR) technique), or by release of the gene by virtue of the action of the restriction enzymes, which cuts the DNA containing the sequence of interest. This first step is equivalent in time to half a day's work.

The DNA fragment released is then sub-cloned in an expression vector by the action of the DNA Ligase enzyme (an operation lasting one night) and the product of the reaction is amplified in a bacterium, after its transformation (one day to obtain bacteria having incorporated plasmid DNA, and one and a half days of obtaining and characterizing the transform ant sought, containing the plasmid coding for the gene of interest).

Moreover, to produce sufficient quantities of the plasmid containing the gene of interest with a view to transformation of the yeast, the bacterial clone obtained in the previous step may be amplified (one night) and the plasmids purified by conventional known methods (one day).

The purified plasmid obtained is then used to transform the selected yeast strain (½ day).

The transformed yeast strain is obtained approximately 4 days after the transformation event.

Consequently, by using the conventional protocols well known to persons skilled in the art, it is possible to obtain a sufficient quantity of yeast transformants for a subsequent study of a gene of interest, for example, for developing a sensitivity or resistance test, the time that elapses between the preparation of the DNA fragment coding for the gene of interest and the obtaining of the yeast strain expressing it is a minimum of 8 days. Moreover, as disclosed above, several techniques are used.

The magnitude of these delays and the multiplicity of the techniques used necessarily give rise to high production costs, incompatible with the development of a rapid sensitivity or resistance test that is simple to implement and inexpensive.

In other words, the prior art methods of obtaining of yeast transformants are undesirable.

The culture of the transformants can be done, for example, in liquid medium and/or solid medium. The medium used in our methods can be any known medium and suitable for the culture of the transformants, for example, minimal synthetic media containing a carbon source such as glucose or galactose and lacking or not a specific nutrient, for example, uracil.

"Qualitative or quantitative analysis" means any analysis of living cells known in the art. For example, it can be a step of counting or scoring the living cells, for example, by measuring the absorbance, for example, at 600 nm of a liquid medium, or by eye counting, by observation when the transformants are cultured, for example, on a solid medium. It can also be, for example, the result of laboratory testing for the sensitivity of the transformants to a test molecule or another method involving the use of a test molecule. For example, it can be a semi-quantitative way based on diffusion (Kirby-Bauer method); small discs containing a test molecule or impregnated paper discs, are dropped in different zones of the culture, for example, onto an agar plate, which is a nutrient-rich environment in which the transformants can grow. The molecule to be tested diffuses in the area surrounding each disc. It can also be, for example, a quantitative way based on dilution: a dilution series of molecule to be tested is established, that is, for example, a series of reaction vials with progressively lower concentrations of molecule substance.

The sensitivity or resistance of protease can be deduced, for example, by measuring the half maximal inhibitory concentration (IC50), by comparing the living number of cells between transformants incubated with molecules and non-incubated with molecules.

Considering the studies on the ability of yeast to repair "broken DNA" (nicked DNA) by the homologous recombination mechanism, we found that, during this cell event, a DNA molecule is repaired at a precise point in its sequence, by putting in place homologous sequences at the "nicking" site and taken within another DNA molecule. By using this physiological phenomenon, it is possible to introduce a defined sequence within the "nicked" DNA provided that the defined sequence is framed on each side by sequences identical to those situated around the "nicking" site.

The minimum size of the homologous sequences present in the two DNA molecules for the recombination event to be able to take place is approximately 30 to 40 pairs of bases.

This technique very advantageously simplifies obtaining the transformants by reducing in particular the number of manipulations which involve a significant reduction in the experimentation time necessary (approximately half compared to known protocols) and in production cost. Use of this technique also enables a large number of samples to be manipulated at the same time.

We provide a detailed description of preferred examples of implementation of our methods below.

EXAMPLE 1

This example of implementation is used for preference when the protease expressed is the isolated protein. When the protease is expressed with all or some of the amino acid sequences situated upstream and downstream of the cleavage site of the protein precursor that contains it, the primers and nucleotide fragments disclosed above will be modified accordingly.

1—Preparation and Modification of the Expression Vector:

The aim of the modification is to be able sub-clone the gene of the protease from virus infecting each infected individual studied and transform the yeast with the protease gene obtained, by a simple and rapid procedure (a single-step procedure).

We created a modified version of the vector pRS316-Gal1/10, which comprises the inducible promoter GAL1/10 in position 5' of the cloning site of the gene to be expressed (Liu H, Krizek J, and Bretscher A. 1992. Construction of a GAL-1 regulated yeast cDNA expression library and its application to the identification of genes whose overexpression causes lethality in yeast. Genetics 132:665-673).

Because of this, the viral gene is expressed when the cell is transformed with this vector in the presence of Galactose and the gene is not expressed when the cells transformed are in the presence of glucose as a carbon source.

For the fragment of amplified viral DNA to be able to be inserted by homologous recombination in the expression vector, the vector must be modified by adding to it, just after the sequence of the inducible promoter, a primer 5' of approximately 40 pairs of bases, followed by a single restriction site (to be able to linearize the vector), and a primer 3' of approximately 40 pairs of bases. Although this modified and linearized vector is a good substrate for the homologous recombination event, the sequence introduced at position 5' (between the gene and the promoter) must not inhibit the transcription of the genes.

To produce the modified version of the expression vector pRS316-Gal 1/10, we exchanged the BamHI-Sac1 fragment of this site with another DNA fragment also framed by the BamH1-Sac1 restriction sites that contain (from 5' to 3'):

the BamH1 restriction site, unique in the vector, followed by
the 35 to 45 nucleotides in the HIV-2 sequence situated just upstream of the protease, followed by
an Not1 restriction site, unique in the vector, followed by
the 35 to 45 nucleotides of the HIV-2 sequence situated just downstream of the protease, followed by
the Sac1 restriction site, unique in the vector.

Modifications to the size of this fragment of approximately 80-90 pairs of bases were carried out to optimize experimental cloning, transformation and expression system. A single modified fragment among 10 different ones that were tested was sufficient for the homologous recombination and expression of the viral protease.

The sequence of this fragment is as follows:

(SEQ ID NO 1)
5'GGATCCGGAGACACCATACAGGGAGCCACCAACAGCGGCCGCAGTA
GAGCCAATAAAAATAATGCTAAAGCGAGCTC 3'

The pRS316-Gal1/10 expression vector thus modified is called pRS316-Gal 1/10M.

2—Choice of the Cell System

Any strain of yeast with auxotrophy markers necessary to allow the selection of the transformant expressing the viral protease, and preferably any strain of *Saccharomyces cerevisiae*.

3—Sub-Cloning of the Proteases of Individuals Affected by the Retrovirus, and Transformation of Yeasts in a Single Step The DNA sequence coding the HIV-2 protease is amplified by the PCR technique, twice.

The first amplification produces a significant quantity of DNA. This reaction takes place using DNA extracted from lymphocytes of the peripheral blood of infected individuals. The nucleotide primers used are of the type:

```
                                            (SEQ ID NO 2)
        Sense primer:
        5'GAAAGAAGCCCCGCAACTTC3'

(SEQ ID NO 3)
        Antisense primer:
        5'GGGATCCATGTCACTTGCCA3'
```

The second amplification frames the protease of an initialization codon of the transcription (ATG) and of a termination codon of the transcription (TAA) and adds on each side the sequences approximately 40 nucleotides that we brought to the vector when it was modified. This PCR reaction takes place on the product of the first PCR with the primers of the type:

```
                                            (SEQ ID NO 4)
Sense primer::
5'CGAGGATCCGGAGACACCATACAGGGAGCCACCAACAGCGGCCGCG
CCATGCCTCAATTC3'

(SEQ ID NO 5)
Antisense primer:
5'GCGGAGCTCGCTTTAGCATTATTTTTATTGGCTCTACTGCGGCCGCTT
AA GATT3'
```

Framing the protease by the initiation and termination codons is that of the isolated protease or the protein comprising all or some of the amino acid sequences situated upstream and downstream of the cleavage site of the precursor in which it is situated.

Figure 2:
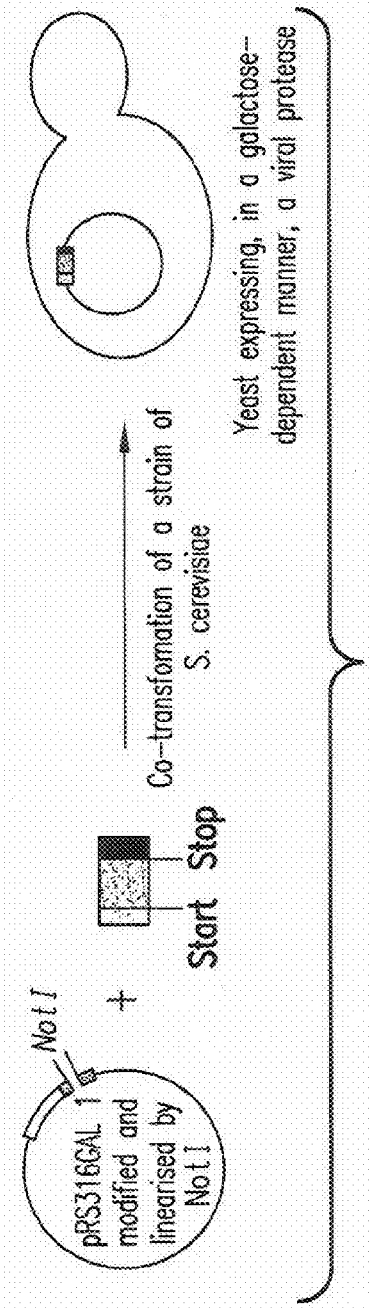

Co-transformation of the pRS316-Gal1/10M vector cleaved by the Not1 restriction enzyme with the product of the second PCR makes it possible, through the homogeneous recombination event that took place in the cell, to obtain a transformed yeast cell carrying the sequence of the HIV-2 protease under the control of the inducible promoter Gal (FIGS. 1 and 2).

4—The Test

A sample of peripheral blood is taken from an individual infected with HIV-2. The lymphocytes issuing from this sampling are purified or not, and their DNA extracted by known methods.

The DNA undergoes the two aforementioned PCR reactions to create the fragment of DNA, carrying the sequence of the protease with or without the or some of the amino-acid sequences situated upstream and downstream of the cleavage site of the precursor in which it is situated and compatible with the expression vector to cause the phenomenon of homogeneous recombination in the transformed cells.

After purification of the product of the second PCR, a yeast strain having a genotype ura3 is co-transformed with the pRS316Gal1/10M linear vector (by its Not1 site).

The transformants potentially producing the protease are recovered on any suitable carrier such as, for example, gelose composed of agar, glucose as a source of carbon, and a synthetic environment with a deficiency of uracil.

Approximately $10^5$ cells, issuing from a single transformant, are deposited and distributed in 12 wells with a 96-well plate and incubated in galactose in the presence of 11 increasing concentrations of each inhibitor to be tested. The twelfth well does not contain any inhibitor.

Figure 3:
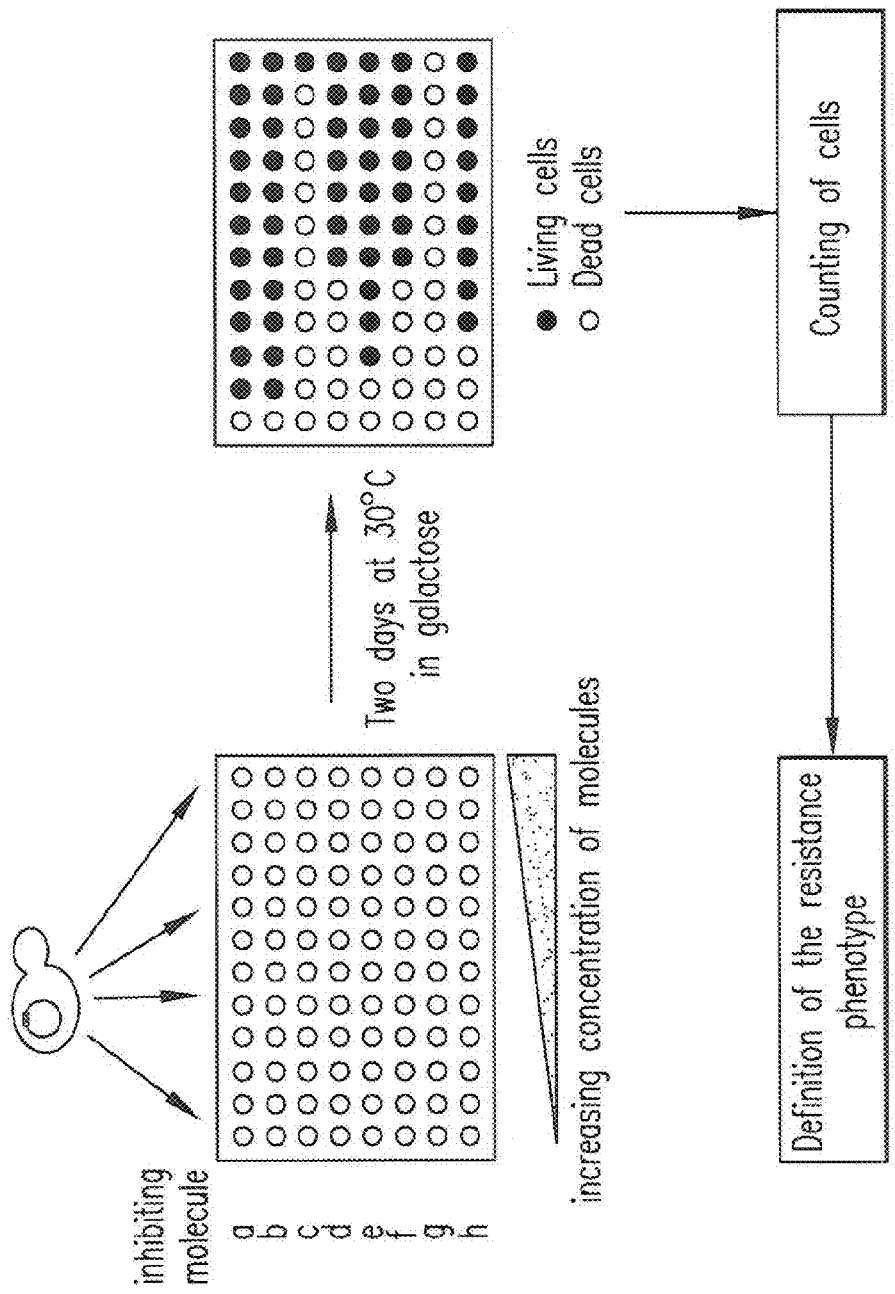
FIG. 3 is a schematic representation of the counting of living and dead cells and a determination of the phenotype.

After 36-48 hours at 30° C., the living cells are counted by a densitometric reading at 600 nm (FIG. 3).

The dose necessary to inhibit half the cell growth under these conditions, compared with the cell growth in the absence of drugs and in the presence of glucose ($IC_{50}$), defines the susceptibility or resistance of this specific strain.

The test was also done on plasma issuing from this sampling, purified or not, and their RNA or DNA extracted by known methods. In this case, these nucleic acids undergo the aforementioned RT-PCR and PCR reactions, if they are of RNA type, and no RT phase if they are of type DNA.

The interval of time between the blood sampling and the definition of the resistance profile is only one week.

EXAMPLE 2

In this example, the expression vector was modified as follows:

A first modified version of the vector pRS316-Gal1/10 was created by exchanging the BamH1-Sac1 fragment of this vector with a DNA fragment, also framed by the BamH1-Sac1 restriction sites that contains (from 5' to 3'):

the BamH1 restriction site, unique in the vector, followed by around 40 nucleotides coding for amino acids situated after the HIV-1 protease coding sequence, followed by a stop condon, followed by a Sac1 restriction site, unique in the vector.

Modifications of the nucleotide sequences coding for amino acids situated after the protease coding sequence were carried out for the experimental cloning, transformation and expression system. Among several modified fragments created and tested for selected homologous recombination and expression of a precursor form of the viral protease, that consists of the protease coding sequence followed by 13 amino acids, one example includes:

```
                                            (SEQ ID NO 56)
GGATCCCTATTGAGACTGTACCAGTAAAATTAAAGCCAGGAATGGATTAA
GAGCTC (for the creation of pRS316-Gal1/10 M-3).
```

A second modified version of the vector pRS316-Gal1/10 was created by exchanging the BamH1-Sac1 fragment of this vector with a DNA fragment, also framed by the BamH1-Sac1 restriction sites that contains (from 5' to 3'):

the BamH1 restriction site, unique in the vector, followed by a start codon, followed by around 20 nucleotides coding for amino acids situated before the HIV-1 protease coding sequence, followed by a Xho1 restriction site, unique in the vector, followed by around 40 nucleotides coding for amino acids situated after the HIV-1 protease coding sequence, followed by a stop codon, followed by a Sac1 restriction site, unique in the vector.

Modifications of the nucleotide sequences coding for amino acids situated before and after the protease coding sequence were carried out for the experimental cloning, transformation and expression system. Among several modified fragments created and tested for selected homologous recombination and expression of a precursor form of the viral protease, in this case the short precursor in the type of SEQ ID NO 15, one example includes:

```
                                            (SEQ ID NO 57)
GGATCCATGTGGGGTAGAGACAACAACTCCCTCGAGTCCTATTGAGACTG
TACCAGTAAAATTAAAGCCAGGAATGGATTAAGAGCTC
(for the creation of pRS316-Gal1/10M-4).
```

2—Choice of the Cell System

Any strain of yeast with necessary auxotrophy markers to allow the selection of the transformant expressing the viral protease, and preferably any strain of *Saccharomyces cerevisiae*. In this example *Saccharomyces cerevisiae* was used.

3—Sub-Cloning of the Proteases of Individuals Affected by the Retrovirus, and Transformation of Yeasts in a Single Step The nucleic acid sequence coding the HIV protease, or any of its precursor forms, were amplified by the RT-PCR technique, followed by a PCR reaction as in Example 1.

The nucleotide primers used for the RT-PCR reaction were of the type:

```
                                            (SEQ ID NO 52)
    Primer5'GP7:       ATGATGACAGCATGTGAGGGAG,
    and (SEQ ID NO 53)
    Primer3'R772:      CCTGAAAATCCATAYAAYAC.
```

The second PCR reaction takes place on the product of the first PCR with either the primers of the type:

```
                                            (SEQ ID NO 55)
Primer R2139S1:  GAGCTCTTAATCCATTCCTGGCTTTAATTTTAC
                 TGGTACAGTTTCAATTGGAC,
and
                                            (SEQ ID NO 58)
Primer5'F-pc-rh: TATACTTTAACGTCAAGGAGAAAAAACCCCGGA
                 TCCATGTGGGGTAGAGACAACAACTCC
``` or the primers of the type:

```
                                            (SEQ ID NO 55)
Primer R2139S1:,
and
                                            (SEQ ID NO 42)
Primer5'F3:      TATACTTTAACGTCAAGGAGAAAAAACCCCGGAT
                 CCTTTAACATGCCTCAGATC.
```

In one case, the co-transformation of the pRS316-Gal1/10M-3 vector cleaved by the BamH1 restriction enzyme with the product of the second PCR, performed with primers SEQ ID NO 42 and 55, makes it possible, through the homologous recombination event that took place in the cell, to obtain a transformed yeast cell, carrying the sequence of a precursor form of the HIV-1 protease that consists of the protease coding sequence followed by 13 amino acids, under the control of the inducible promoter Gal.

In the other case, co-transformation of the pRS316-Gal1/10M4 vector cleaved by the Xho1 restriction enzyme with the product of the second PCR, performed with primers SEQ ID NO 54 and 55, makes it possible, through the homologous recombination event that took place in the cell, to obtain a transformed yeast cell, carrying the sequence of a precursor form of the HIV-1 protease (like SEQ ID NO 15) under the control of the inducible promoter Gal.

4—The Test

A sample of peripheral blood is taken from an individual infected with HIV-1. The plasma or lymphocytes issuing from this sampling are purified or not, and their RNA or DNA extracted by known extraction kits, like Q1Aamp Viral RNA Mini Kit from QIAGEN (The Netherlands).

These viral nucleic acids undergo the same treatments as defined in Example 1, to amplify the DNA sequence coding for the protease precursor.

After purification of the product of the second PCR, a yeast strain having a genotype ura3 is either co-transformed with the pRS316Gal1/10M-3 linear vector (by its BamH1 site) or co-transformed with the pRS316Gal1/10M-4 linear vector (by its Xho1 site).

The transformants potentially producing the protease are recovered on any suitable carrier such as gelose composed of agar, glucose as a source of carbon, and a synthetic environment with a deficiency of uracil.

Approximately $10^5$ cells, issuing from a single transformant, are deposited and distributed in 12 wells with a 96-well plate and incubated either in liquid or solid galactose containing media in the presence of at least 8 increasing concentrations of each inhibitor to be tested. One well does not contain any inhibitor.

After 36 to 48 hours at 30° C., the living cells are counted by a densitometric reading at 600 nm (FIG. 4) when the test was performed in liquid media or by eye when the test was performed in solid media.

The dose necessary for inhibiting half the cell growth under these conditions, compared with the cell growth in the absence of drugs and in the presence of glucose ($IC_{50}$), defines the susceptibility or resistance of this specific strain.

The interval of time between blood sampling and definition of the resistance profile is only one week.

EXAMPLE 3

Example of Protease Sequences Amplifications

1—Integral Protease Precursor Sequence

The integral protease precursor sequence was amplified by PCR from the laboratory viral pNL4.3 DNA strain with using the following primers:

```
                                         (SEQ ID NO 38)
5' Primer F-GagPol GCGGAGTCTAGAAGGAGAGAGATGGGTGCG
                   AGA,
and (SEQ ID NO 39)
3' Primer R-GagPol CTAATCTTTCTCGAGTGTTAATCCTCATCCTG
                   TCTACTTG.
```

The used PCR program was as follows:
3 min at 95° C., followed by 35 cycles of
1 min at 95° C., 30 seconds at 55° C., 2 min at 72° C., and finished with one round of 7 min at 72° C.

The PCR product (SEQ ID NO 18) was purified by standard procedures digested by restriction enzyme XbaI (Invitrogen, USA), following the manufacturing recommendations and introduced, through overnight DNA ligation (T4 DNA Ligase from Gibco USA), as manufacturing recommendations into previously XbaI digested pRS316-Gal/10 vector.

2—Protease Precursor Sequence Starting at the Beginning of the Protease Coding Sequence and Ending at the End of the Pol Coding Region (SEQ NO 37)

The PCR reaction was performed on purified DNA construct in pRS316-Gal/10 vector obtained in Item 1. PCR conditions and other experiences were the same as conditions described in previous Item 1.

The protease precursor sequence from protease coding sequence until the end of the gag-pol coding sequence was obtained using the following primers:

```
                                         (SEQ ID NO 42)
5' Primer F3:    TATACTTTAACGTCAAGGAGAAAAAACCCCGGAT
                 CCTTTAACATGCCTCAGATC,
and (SEQ ID NO 43)
3' Primer M13F:  GTTTTCCCAGTCACCACG for the
                 amplification step.
```

The primers were selected to provide sequences situated on both sides of the cloning site in the expression vector.

Co-transformation of linear pRS316-Gal1/10 vector (digested with BamH1) with PCR product produced, by a recombination event in the cell, a transformed yeast carrying the precursor sequence under the control of inducible Gal promoter.

3—Different Size of Protease Precursor Sequence

In this example the construct obtained in previous Item 2 was used.

Plasmid containing the gag-pol precursor sequences starting at the protease and ending at the end of the pol region was linearized by digestion with restriction enzyme Xho1 (Invitrogen, USA) according to manufacturing recommendations.

After, 6 micrograms of the linearized plasmid were digested with 1 unit of Bal31 exonuclease enzyme (BioLabs, USA) at 30° C. following the manufacturing recommendations. Equal aliquots were taken every 20 minutes during 2 hours incubation, and the reaction was stopped with 25 mM EDTA. This produced a DNA partial digest and fragments of different size. These fragments, present in each Bal31 digestion aliquot, were ligated to the following double strand oligonucleotides in a ratio of 50 pmoles oligonucleotide to 1 microgram DNA:

```
                                         (SEQ ID NO 44)
sens Gal-gp-rh:     TATACTTTAACGTCAAGGAGAAAAAACCCC
                    GGATCCATGTACGATGTACGATG (SEQ ID NO 45)
antisens Gal-gp-rh: ATATGAAATTGCAGTTCCTCTTTTTTGGG
                    GCCTAGGTACATGCTACATGCTAC (SEQ ID NO 46)
sens M13-gp-rh:     TAATAGGTAATAGGTAAGAGCTCCAATTCG
                    CCCTATAGTGAGTCGTATTACAAT (SEQ ID NO 47)
Antisens M13-gp-rh: ATTATCCATTATCCATTCTCGAGGTTAA
                    GCGGGATATCACTCAGCATAATGTTA.
```

These oligonucleotides further contain initiation and termination codons and identical sequences to the pRS316-Gal1/10 vector.

The co-transformation of linearized pRS316-Gal1/10 vector by BamH1-Sac1 enzymes with the ligation product previously digested with Kpn1 restriction enzyme (Invitrogen, USA), following the recommendation of manufacturer produce, by homologous recombination done in cell, a library of transformed yeasts carrying each one C terminal deleted forms of the gag-pol precursor starting at the protease sequence under the control of inducible promoter Gal.

4—A Truncated Protease Precursor Sequence Comprising a Single Mutation (Addition of a Single A Nucleotide) to Mimic the Natural Open Reading Frame Shift of the Gag-Pol Gene Transcription The PCR conditions and other experiments were the same as conditions described in previous Item 1.

A mutated precursor sequence containing an additional A nucleotide at position 1638 was made. The primers used for the PCR reaction were:

```
                                           (SEQ ID NO 49)
primer 5'-a435:   CAGGCTAATTTTTTAAGGG, (SEQ ID NO 50)
primer R-a435:    CCCTTAAAAAATTAGCCTG, (SEQ ID NO 51)
primer F1071B1:   GGATCCATGATGACAGCATGTCAGGGAGTGGGAG
                  GACCCGGCCATAAGGCAAGAGTTTTG,
and (SEQ ID NO 55)
primer R2139S1:   GAGCTCTTAATCCATTCCTGGCTTTAATTTT
                  ACTGGTACAGTTTCAATTGGAC.
```

The mutated precursor was made in two steps of PCR. In a first PCR, 2 independent reactions, using as template the construct obtained in previous Item 2, involved pairs of primers, SEQ ID NO 49 and SEQ ID NO 55 for one and SEQ ID NO 50 and SEQ ID NO 51 for the second, to introduce a further A (Adenine) at position 1638 of the sequence.

These two PCR products were mixed and diluted to be a template for the second PCR which was realized with primers SEQ ID NO 51 and SEQ ID NO 55. The newly obtained DNA fragment was digested with BamH1 and Sac1 restriction enzymes (Invitrogen, USA and Fermentas, Canada, respectively), following recommendations of the manufacturer, and ligated with T4 DNA Ligase, (Gibso, USA) following recommendations of the manufacturer, in pRS316-Gal1/10 vector previously digested with BamH1 and Sac1 restriction enzymes (Invitrogen, USA and Fermentas, Canada, respectively), following recommendations of the manufacturer.

5—Cloning a Precursor Sequence of HIV-1 Protease from Infected Patient

An HIV-1 protease precursor form coding sequence was amplified from purified total RNA extracted from blood plasma of infected patients by RT-PCR followed by a PCR reaction, as described in Example 2.

The primers used for the RT-PCR reaction were:

```
                                           (SEQ ID NO 52)
Primer 5' GP7:    ATGATGACAGCATGTGAGGGAG,
and (SEQ ID NO 53)
Primer 3' R772:   CCTGAAAATCCATAYAAYAC.
```

The second amplification frames the protease between an initialization codon of the transcription (ATG) and a termination codon of the transcription (TAA). ATG was situated 70 nucleotides above of the first codon of the protease. TAA was situated 150 nucleotides below of the last codon. Moreover, the second amplification adds on both sides sequences corresponding to the vector to clone it in yeast by homologous recombination. This PCR was made on the first PCR product with the following primers:

```
                                           (SEQ ID NO 55)
Primer R2139S1:   GAGCTCTTAATCCATTCCTGGCTTTAATTTTA
                  CTGGTACAGTTTCAATTGGAC,
and (SEQ ID NO 54)
Primer 5' F-pc-rh: ATACTTTAACGTCAAGGAGAAAAAACCCCGGA
                   TCCATGTGGGGTAGAGACAACAACTCC.
```

EXAMPLE 4

Example of Determining the Resistance/Sensitive Character of a Protease from HIV-1 Infected Individual An HIV-1 short protease precursor form, of the size of SEQ ID NO 15, coding sequence was amplified by RT-PCR followed by a PCR reaction, as described in Example 2, from purified total RNA extracted from blood plasma of an infected patient, namely P#10, known to carry HIV-1 strains resistant to protease inhibitors like lopinavir, saquinavir and darunavir.

The followed procedure was as described in Example 3 (5), using the following primers:

```
                                           (SEQ ID NO 52)
Primer 5' GP7:    ATGATGACAGCATGTGAGGGAG,
and (SEQ ID NO 53)
Primer 3' R772:   CCTGAAAATCCATAYAAYAC, for the
                  RT-PCR step, and the primers:

(SEQ ID NO 55)
Primer R2139S1:   GAGCTCTTAATCCATTCCTGGCTTTAATTTT
                  ACTGGTACAGTTTCAATTGGAC,
and (SEQ ID NO 54)
Primer 5' F-pc-rh: ATACTTTAACGTCAAGGAGAAAAAACCCCGGA
                   TCCATGTGGGGTAGAGACAACAACTCC, for
                   the second amplification.
```

The obtained final PCR product was cloned into pRS316-Gal1/10M-4 by the co-transforming single step procedure described in Example 2 (3). The transformed yeast cell was of the strain BY4741 (Euroscarf, Germany) having the following genotype: MATa, his3Δ1, leu2Δ0, met15Δ0, ura3Δ0.

To define the ability of lopinavir, saquinavir and darunavir molecules to inhibit the cloned protease, hence the resistance pattern, the procedure described in Example 3 (5) was performed to obtain yeast cells expressing sensitive and resistant proteases. The sensitive or resistant character of the cloned protease was determined in liquid and in solid media.

When the resistance test was performed in liquid media, the higher concentration of the molecules tested were:
50 microMolar for lopinavir,
100 microMolar for darunavir,
400 microMolar for saquinavir, 7 serial dilutions, one to one, of those solutions were present in the test.

In parallel, the same procedure was followed to test the ability of the same protease inhibitors to act on the short protease precursor form (SEQ ID NO 15) expressed in BY4741 yeast transformants. In this case, the DNA amplification was performed, on purified pNL4.3 plasmid carrying the total sensitive strain HIV-1 genome, by a PCR reaction using the following primers:

```
                        (SEQ ID NO 55)
Primer R2139S1:  GAGCTCTTAATCCATTCCTGGCTTTAATTTTA
                 CTGGTACAGTTTCAATTGGAC,
and
                        (SEQ ID NO 54)
Primer 5' F-pc-rh: ATACTTTAACGTCAAGGAGAAAAAACCCCGGA
                   TCCATGTGGGGTAGAGACAACAACTCC.
```

Figure 5A:
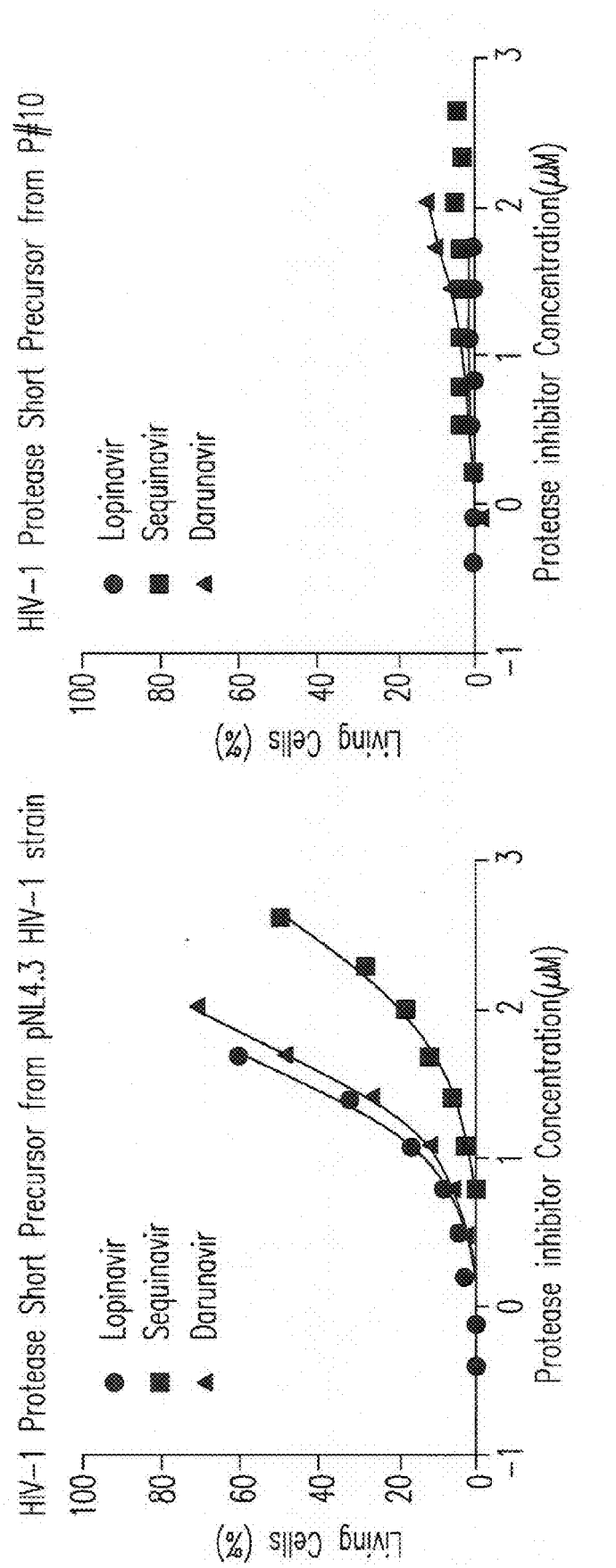
FIG. 5a shows a pair of graphs of percentage of living cells as a function of inhibitor concentration.

The obtained results, presented as the percentage of living cells as a function of the inhibitor concentration in FIG. 5a, show:
  i) lack of inhibition, by the three inhibiting molecules tested, of the viral protease in its precursor context amplified from patient P#10,
  ii) inhibition, by the three inhibiting molecules tested, of a sensitive viral protease in its precursor context amplified from a wild HIV-1 strain, namely pNL4.3.

The data was processed by the software GraphPad Prism v5.0 (GraphPad Inc, USA) to obtain the corresponding IC50 values that are showed in Table 1:

TABLE 1

| Protease Inhibitor | IC50 (microMolar) | |
| --- | --- | --- |
| | PNL4.3 protease | P#10 protease |
| Lopinavir | 39.2 | >$10^5$ |
| Darunavir | 50.5 | 1907.0 |
| Saquinavir | 433.2 | >$10^5$ |

Therefore, the viral protease from patient P#10 is resistant to the tested inhibitor molecules.

Figure 5B:
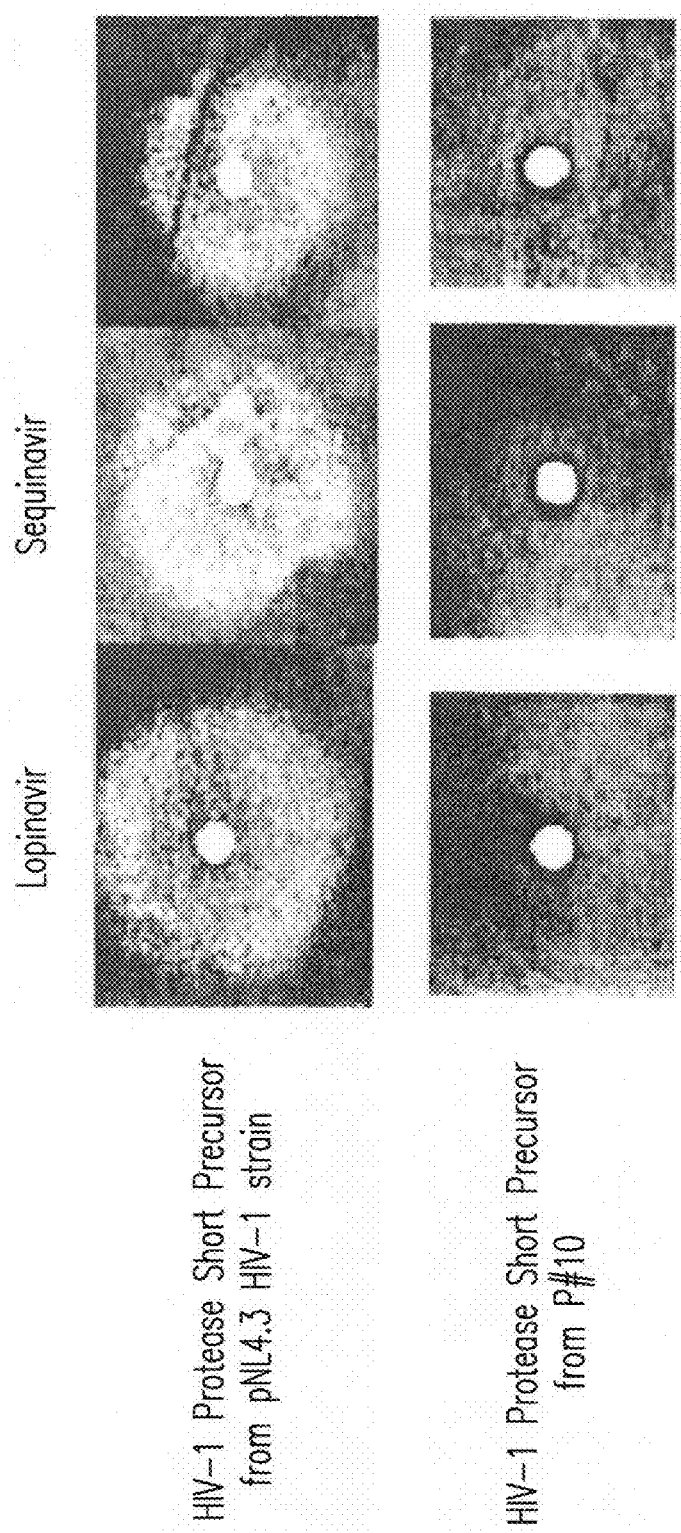
FIG. 5b shows photos of cell growth as a function of resistance to inhibitor.

When the resistance test was performed in solid media, the yeast transformant expressing each viral protease was plated on synthetic minimal media, agar plate, in the presence of 2% Galactose. A 5 mm diameter paper disk (Mini-trans-Blot, Bio-Rad USA) impregnated with 10 microliters of either 0.5 milliMolar lopinavir, 0.5 m milliMolar darunavir, or 1 milliMolar saquinavir, was placed in the center of the plate. After 3 days at 30° C. observation by naked eye was performed. When the expressed viral protease was sensitive to the inhibitor, a halo of growing cells was observed, whereas no growing cells were observed when the viral protease expressed in transformed yeasts were resistant to inhibitor (FIG. 5b).

As demonstrated in this example, the method allows determination of the sensitivity or resistance of isolate of HIV retrovirus to molecules.

EXAMPLE 5

Diagnostic Kit for Resistance to Retroviruses

A diagnostic kit also determines the sensitivity or resistance of retrovirus isolates to therapeutic retroviral treatments based on inhibitors of the viral protease. It may comprise:

nucleotide primers and, for example, nucleotide primers as previously disclosed for implementation of the amplification of DNA coding for the retrovirus protease by the PCR technique, namely:
for the first amplification primers of the type:

```
                                    (SEQ ID NO 2)
Sense primer:      5'GAAAGAAGCCCCGCAACTTC3'

(SEQ ID NO 3)
Antisense primer:  'GGGATCCATGTCACTTGCCA3'
``` for the second amplification, primers of the type:

```
                                    (SEQ ID NO 4)
Sense primer:      5'CGAGGATCCGGAGACACCATACAGGGAGCC
                    ACCAACAGCGGCCGCGCCATGCCTCAATTC3'

(SEQ ID NO 5)
Antisense primer:  5'GCGGAGCTCGCTTTAGCATTATTTTTA
                    TTGGCTCTACTGCGGCCGCTTAA GATT3'
                    and/or primers selected from the
                    group comprising SEQ ID NO 38,
                    39, 40, 41, 42, 48, 51 to 58;
``` at least one expression vector and, for example, the plasmid modified and linearized according to our methods and as previously described, for example, the plasmid pRS316-Gal1/10M, M-3, M-4;

at least one strain of yeast with the necessary auxotrophy marker to permit selection of the transformant expressing the viral protease, and preferably a strain of Saccharomyces cerevisiae; and at least one multi-well plate or any other suitable support.

Naturally, when amplification is carried out on the RNA or DNA coding for the protease of the retrovirus with all or some of the amino acid sequences situated upstream and downstream of the cleavage site of the protein precursor that contains it, the primers and nucleotide fragments will be modified accordingly.

Figure 4:
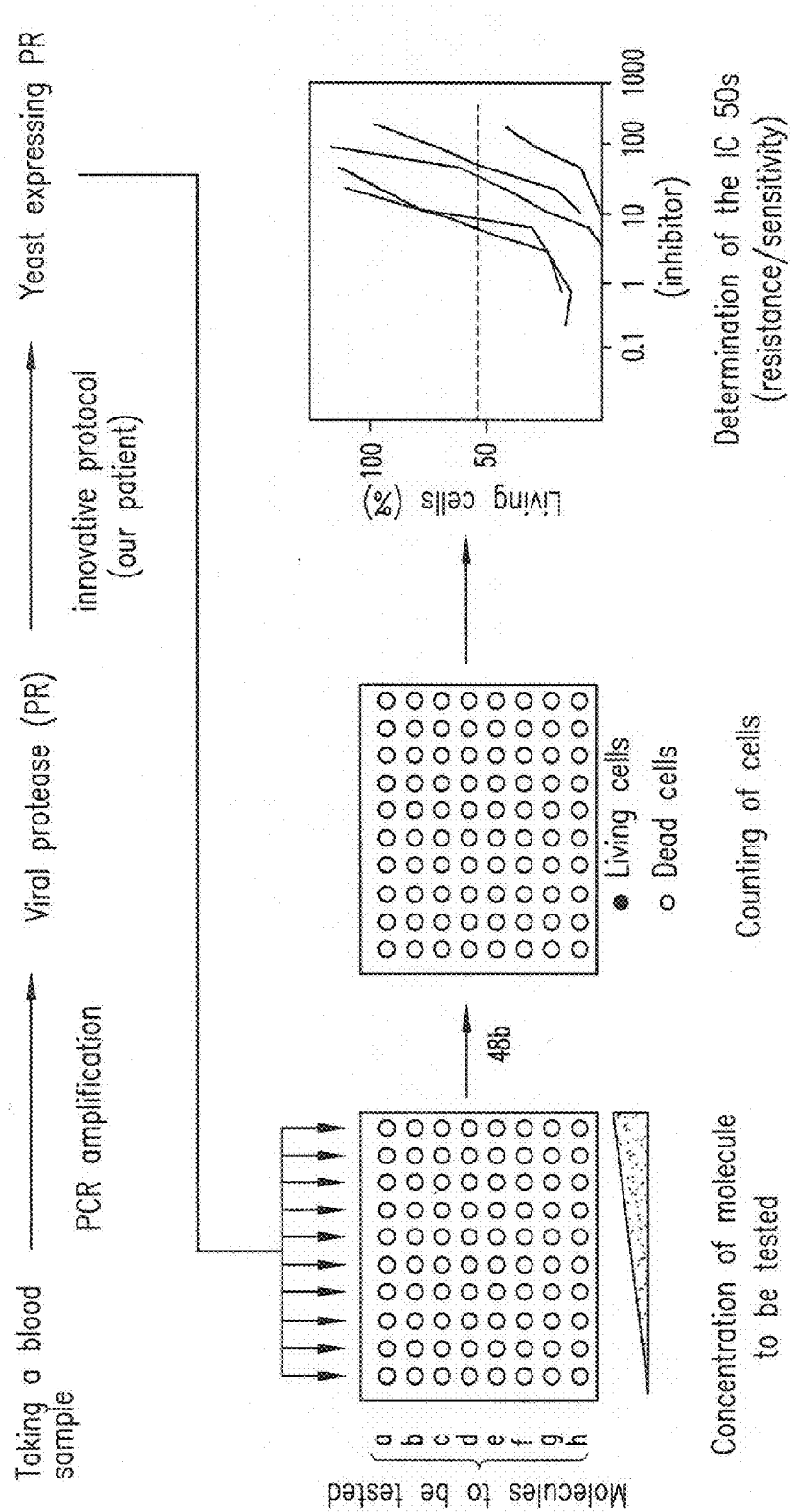
FIG. 4 is a schematic representation of a diagnostic kit.

A principle of the kit, also illustrated in FIG. 4, is as follows:
  Using the blood of the patient, the gene coding for the viral protease is amplified by an RT-PCR reaction with the primers described in the method and supplied in the kit.
  Amplification of the gene of the viral protease using cell DNA is also possible.
  The amplified product and the modified and linearized vector (also supplied in the kit) are used for transforming a strain of yeast, also supplied in the kit, in a multi-well plate.
  In a preferred, though in no way limiting fashion, after incubation at 30° in a dry oven in a selective medium containing glucose, 2 microliters of the cell suspension are transferred to a new plate, supplied in the kit, containing increasing concentrations of each active principle used in therapy. 300 microliters of the selected medium containing galactose are added to each well, before incubating at to 30° C. in a dry oven for 36-48 hours.
  At the end of incubation, for example, if the support was liquid media, the living cells are counted by a densitometric reading at 600 nm. The dose necessary for inhibiting half the cell growth, compared with the cell growth of the strain of yeast not expressing the viral protease, defines the $IC_{50}$ for each inhibitor. A comparison between the $IC_{50}$s obtained and those of a reference wild protease makes it possible to determine any resistance phenotype.

At the end of incubation, for example, if the support is solid as in Example 4, naked eye observation defines the HIV protease sensitive/resistant character towards a molecule, for example, a specific inhibitor of the viral protease from the infected individual, by merely determining whether there is growth (sensitive) or no growth (resistant) of the transformed yeast.

The interval of time between the taking of blood and the definition of the resistance profile is only one week.

Although our and methods have been described in connection with specific forms thereof, it will be appreciated that a wide variety of equivalents may be substituted for the specified elements/steps described herein without departing from the spirit and scope of this disclosure as described in the appended claims.

Also, this disclosure refers to and identifies various publications. The subject matter of those publications is incorporated herein by reference.

The invention claimed is:

1. A method for measuring functional activity of an HIV-1 protease in infected patients in response to an antiviral agent in a phenotypic assay comprising:
   a) amplifying sequences coding for an HIV-1 protease from purified total RNA extracted from an HIV-1 infected patient, said sequences having a formula A-B-C, wherein
   B is a sequence encoding for the HIV-1 protease, as obtained after the cleavage of the Gag-Pol precursor at the first p6$^{pol}$↓PR and the second PR↓RT/p51 cleavage sites,
   A corresponds to SEQ ID NO: 59, a consensus sequence $X_1VSFX_2X_3$, wherein $X_1$ is M or T, $X_2$ is N or S and $X_3$ is F or L encoding for the 6 amino acids preceding in the Gag-Pol precursor the sequence B as previously defined, and
   C is a sequence encoding for at least the first amino acid following in the Gag-Pol precursor the sequence B, said at least first amino acid being a proline residue,
   wherein the said two cleavage sites and the HIV-1 protease are originated from an HIV-1 isolate,
   b) recombining fragments of DNA which are a final product of the amplification of step a), and an expression vector allowing expression of sequence coding for the HIV-1 protease from the infected patient to be studied under control of a known inducible promoter through co-transformation of the vector and the DNA fragments with at least one yeast cell,
   c) culturing co-transformed yeast cell or cells to obtain a sufficient number of transformants to measure the functional activity of an HIV-1 protease, and recovering transformants issuing from the co-transformed cell, on any suitable medium,
   d) incubating the transformants in liquid or solid inducer containing media in the presence or in the absence of an antiviral agent to be tested, wherein said inducer allows the expression of an HIV-1 protease,
   e) qualitatively or quantitatively analyzing the living yeast cells, and
   f) deducing the ability of the antiviral agent to inhibit an HIV-1 protease activity, by comparing the living number of yeast cells between the antiviral agent treated and untreated transformants,
   wherein the living number of yeast cells is a function of the efficiency of the antiviral agent to inhibit an HIV-1protease activity.

2. The method according to claim 1, comprising before step a), extracting nucleic acids from i) cells infected by a retrovirus and/or ii) body fluids from infected animals, and/or iii) blood from infected animals, and/or iv) infected culture cell media.

3. The method according to claim 2, wherein the nucleic acid is DNA and/or RNA.

4. The method according to claim 2, wherein the nucleic acids are extracted from cells taken from an individual or an animal infected by a retrovirus and/or ii) body fluids from infected animals, and/or iii) blood from infected animals, and/or iv) infected culture cell media.

5. The method according to claim 1, wherein the antiviral agent are at least one selected from the group consisting of molecules of a library, chemical molecules, natural molecules and molecules extracted from plants.

6. The method according to claim 1, wherein the antiviral agents are at least one selected from the group consisting of chemical molecules having an inhibiting activity on the HIV-1 protease, therapeutic treatments based on inhibitors of the HIV-1 protease.

7. The method according to claim 1, wherein the incubation is performed with an increasing concentration of antiviral agents.

8. The method according to claim 1, wherein said HIV-1 protease is encoded by a nucleic acid sequence selected from the group consisting of SEQ ID NO: 10, SEQ ID NO: 11, SEQ ID NO: 12, SEQ ID NO: 13, SEQ ID NO: 14, and SEQ ID NO: 15.

9. The method according to claim 1, wherein the expression vector is plasmid pRS316-Gal1/10.

10. The method according to claim 8, wherein the expression vector is plasmid pRS316-Gal1/10 comprising inducible promoter Gal1/10 in position 5' of a cloning site of a gene to be expressed, and in which a fragment BamH1-Sac1 is replaced by another fragment of DNA consisting of (from 5' to 3'):

the BamH1 restriction site, unique in the vector, followed by about 20 nucleotides in a retrovirus sequence situated just upstream of the protease, followed by a restriction site, unique in the vector, followed by 0 to 2511 nucleotides of the retrovirus sequence situated downstream of the protease, followed by the Sac1 restriction site, unique in the vector.

11. The method according to claim 1, wherein the yeast is Saccharomyces cerevisiae.

12. The method according to claim 1, wherein the culture medium of the co-transformed yeast cells is deficient in glucose.

13. The method according to claim 1, wherein incubation of the transformant is done in galactose containing media.

\* \* \* \* \*

```
                              SEQUENCE LISTING

<160> NUMBER OF SEQ ID NOS: 59

<210> SEQ ID NO 1
    <211> LENGTH: 77
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 1
ggatccggag acaccataca gggagccacc aacagcggcc gcagtagagc caataaaaat        60
aatgctaaag cgagctc                                                       77

<210> SEQ ID NO 2
    <211> LENGTH: 20
    <212> TYPE: DNA
    <213> ORGANISM: Artificial Sequence
    <220> FEATURE:
    <223> OTHER INFORMATION: Description of Artificial Sequence: Synthetic
          primer

<400> SEQUENCE: 2
gaaagaagcc ccgcaacttc                                                    20

<210> SEQ ID NO 3
    <211> LENGTH: 20
    <212> TYPE: DNA
    <213> ORGANISM: Artificial Sequence
    <220> FEATURE:
    <223> OTHER INFORMATION: Description of Artificial Sequence: Synthetic
          primer

<400> SEQUENCE: 3
gggatccatg tcacttgcca                                                    20

<210> SEQ ID NO 4
    <211> LENGTH: 60
    <212> TYPE: DNA
    <213> ORGANISM: Artificial Sequence
    <220> FEATURE:
    <223> OTHER INFORMATION: Description of Artificial Sequence: Synthetic
          primer

<400> SEQUENCE: 4
cgaggatccg gagacaccat acagggagcc accaacagcg gccgcgccat gcctcaattc        60

<210> SEQ ID NO 5
    <211> LENGTH: 54
    <212> TYPE: DNA
    <213> ORGANISM: Artificial Sequence
    <220> FEATURE:
    <223> OTHER INFORMATION: Description of Artificial Sequence: Synthetic
          primer
```

<400> SEQUENCE: 5
gcggagctcg ctttagcatt attttttattg gctctactgc ggccgcttaa gatt        54

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggatccggag acaccataca gggagccacc aacagcggcc        40

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcagtagagc aataaaaaat aatgctaaag cgagctc        37

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcggagctcg ctttagcatt attttttattg gctactgcgg ccgcttaaga tt        52

<210> SEQ ID NO 9
<211> LENGTH: 303
<212> TYPE: DNA
<213> ORGANISM: Artificial Sequence
<220> FEATURE:
<223> OTHER INFORMATION: Description of Artificial Sequence: Synthetic
      HIV protease sequence containing start (ATG) and stop (TAA) codons

<400> SEQUENCE: 9
atgcctcaga tcactctttg gcagcgaccc ctcgtcacaa taaagatagg ggggcaatta        60
aaggaagctc tattagatac aggagcagat gatacagtat tagaagaaat gaatttgcca       120
ggaagatgga aaccaaaaat gatagggggaa attggaggtt ttatcaaagt aagacagtat       180
gatcagatac tcatagaaat ctgcggacat aaagctatag gtacagtatt agtaggacct       240
acacctgtca acataattgg aagaaatctg ttgactcaga ttggctgcac tttaaatttt       300
taa                                                                     303

<210> SEQ ID NO 10
<211> LENGTH: 324
<212> TYPE: DNA
<213> ORGANISM: Artificial Sequence
<220> FEATURE:
<223> OTHER INFORMATION: Description of Artificial Sequence: Synthetic
      HIV-1 protease sequence with 24 more nucleic acids at its 5' end,
      3 more nucleic acids at its 3' end

<400> SEQUENCE: 10
ggatccatgg tatcctttaa cttccctcag atcactcttt ggcagcgacc cctcgtcaca        60

```
ataaagatag gggggcaatt aaaggaagct ctattagata caggagcaga tgatacagta    120
ttagaagaaa tgaatttgcc aggaagatgg aaaccaaaaa tgataggggg aattggaggt    180
tttatcaaag taagacagta tgatcagata ctcatagaaa tctgcggaca taaagctata    240
ggtacagtat tagtaggacc tacacctgtc aacataattg gaagaaatct gttgactcag    300
attggctgca ctttaaattt tccc                                          324
```

<210> SEQ ID NO 11
<211> LENGTH: 381
<212> TYPE: DNA
<213> ORGANISM: Artificial Sequence
<220> FEATURE:
<223> OTHER INFORMATION: Description of Artificial Sequence: Synthetic
      HIV-1 protease sequence with 24 more nucleic acids at its 5' end,
      60 more nucleic acids in its 3' end

<400> SEQUENCE: 11

```
ggatccatgg tatcctttaa cttgcctcag atcactcttt ggcagcgacc cctcgtcaca     60
ataaagatag gggggcaatt aaaggaagct ctattagata caggagcaga tgatacagta    120
ttagaagaaa tgaatttgcc aggaagatgg aaaccaaaaa tgataggggg aattggaggt    180
tttatcaaag taagacagta tgatcagata ctcatagaaa tctgcggaca taaagctata    240
ggtacagtat tagtaggacc tacacctgtc aacataattg gaagaaatct gttgactcag    300
attggctgca ctttaaattt tcccattagt ccaattgaaa ctgtaccagt aaaattaaag    360
ccaggaatgg attaagagct c                                             381
```

<210> SEQ ID NO 12
<211> LENGTH: 327
<212> TYPE: DNA
<213> ORGANISM: Artificial Sequence
<220> FEATURE:
<223> OTHER INFORMATION: Description of Artificial Sequence: Synthetic
      HIV-1 protease sequence with 27 more nucleic acids at its 5' end,
      3 more nucleic acids in its 3' end

<400> SEQUENCE: 12

```
ggatccatga ctgtatcctt taacttccct cagatcactc tttggcagcg acccctcgtc     60
acaataaaga tagggggggca attaaaggaa gctctattag atacaggagc agatgataca    120
gtattagaag aaatgaattt gccaggaaga tggaaaccaa aatgatagg gggaattgga    180 ggttttatca agtaagaca gtatgatcag atactcatag aaatctgcgg acataaagct    240
ataggtacag tattagtagg acctacacct gtcaacataa ttggaagaaa tctgttgact    300
cagattggct gcactttaaa ttttccc                                        327
```

<210> SEQ ID NO 13
<211> LENGTH: 384
<212> TYPE: DNA
<213> ORGANISM: Artificial Sequence
<220> FEATURE:
<223> OTHER INFORMATION: Description of Artificial Sequence: Synthetic
      HIV-1 protease sequence with 27 more nucleic acids at its 5' end,
      60 more nucleic acids in its 3' end

<400> SEQUENCE: 13

```
ggatccatga ctgtatcctt taacttgcct cagatcactc tttggcagcg acccctcgtc     60
acaataaaga tagggggggca attaaaggaa gctctattag atacaggagc agatgataca    120
gtattagaag aaatgaattt gccaggaaga tggaaaccaa aatgatagg gggaattgga    180
```

```
ggttttatca aagtaagaca gtatgatcag atactcatag aaatctgcgg acataaagct        240
ataggtacag tattagtagg acctacacct gtcaacataa ttggaagaaa tctgttgact        300
cagattggct gcactttaaa ttttcccatt agtccaattg aaactgtacc agtaaaatta        360
aagccaggaa tggattaaga gctc                                               384
```

<210> SEQ ID NO 14
<211> LENGTH: 387
<212> TYPE: DNA
<213> ORGANISM: Artificial Sequence
<220> FEATURE:
<223> OTHER INFORMATION: Description of Artificial Sequence: Synthetic
      HIV-1 protease sequence with 30 more nucleic acids at its 5' end,
      60 more in its 3' end

<400> SEQUENCE: 14

```
ggatccatgg gaactgtatc ctttaacttg cctcagatca ctctttggca gcgacccctc         60
gtcacaataa agatagggggg gcaattaaag gaagctctat tagatacagg agcagatgat       120
acagtattag aagaaatgaa tttgccagga agatggaaac caaaaatgat aggggggaatt       180 ggaggtttta tcaaagtaag acagtatgat cagatactca tagaaatctg cggacataaa       240
gctataggta cagtattagt aggacctaca cctgtcaaca taattggaag aaatctgttg       300
actcagattg gctgcacttt aaattttccc attagtccaa tgaaactgt accagtaaaa        360 ttaaagccag gaatggatta agagctc                                           387
```

<210> SEQ ID NO 15
<211> LENGTH: 435
<212> TYPE: DNA
<213> ORGANISM: Artificial Sequence
<220> FEATURE:
<223> OTHER INFORMATION: Description of Artificial Sequence: Synthetic
      HIV-1 short precursor sequence

<400> SEQUENCE: 15

```
ggatccatgt ggggtagaga caacaactcc ctctcagaag caggagccga tagacaagga         60
actgtatcct ttagcttccc tcagatcact ctttggcagc gacccctcgt cacaataaag       120 atagggggc aattaaagga agctctatta gatacaggag cagatgatac agtattagaa       180
gaaatgaatt tgccaggaag atggaaacca aaaatgatag ggggaattgg aggttttatc       240
aaagtaagac agtatgatca gatactcata gaaatctgcg gacataaagc tataggtaca       300
gtattagtag gacctacacc tgtcaacata attggaagaa atctgttgac tcagattggc       360 tgcacttaa attttcccat tagtccaatt gaaactgtac cagtaaaatt aaagccagga       420
atggattaag agctc                                                        435
```

<210> SEQ ID NO 16
<211> LENGTH: 435
<212> TYPE: DNA
<213> ORGANISM: Artificial Sequence
<220> FEATURE:
<223> OTHER INFORMATION: Description of Artificial Sequence: Synthetic
      HIV-1 short precursor sequence with cleavage site mutation
      downstream the protease coding sequence

<400> SEQUENCE: 16

```
ggatccatgt ggggtagaga caacaactcc ctctcagaag caggagccga tagacaagga         60
actgtatcct ttagcttccc tcagatcact ctttggcagc gacccctcgt cacaataaag       120 atagggggc aattaaagga agctctatta gatacaggag cagatgatac agtattagaa       180
```

| | |
|---|---|
| gaaatgaatt tgccaggaag atggaaacca aaaatgatag ggggaattgg aggttttatc | 240 |
| aaagtaagac agtatgatca gatactcata gaaatctgcg gacataaagc tataggtaca | 300 |
| gtattagtag gacctacacc tgtcaacata attggaagaa atctgttgac tcagattggc | 360 |
| tgcactttaa atattcccat tagtccaatt gaaactgtac cagtaaaatt aaagccagga | 420 |
| atggattaag agctc | 435 |

<210> SEQ ID NO 17
<211> LENGTH: 792
<212> TYPE: DNA
<213> ORGANISM: Artificial Sequence
<220> FEATURE:
<223> OTHER INFORMATION: Description of Artificial Sequence: Synthetic
    HIV-1 long precursor sequence with modification of the open
    reading frame

<400> SEQUENCE: 17

| | |
|---|---|
| ggatccatga tgacagcatg tcagggagtg gggggacccg gccataaagc aagagttttg | 60 |
| gctgaagcaa tgagccaagt aacaaatcca gctaccataa tgatacagaa aggcaatttt | 120 |
| aggaaccaaa gaaagactgt taagtgtttc aattgtggca agaagggca catagccaaa | 180 |
| aattgcaggg cccctaggaa aaagggctgt tggaaatgtg gaaggaagg acaccaaatg | 240 |
| aaagattgta ctgagagaca ggctaatttt ttaagggaag atctggcctt cccacaaggg | 300 |
| aaggccaggg aatttcttc agagcagacc agagccaaca gccccaccag aagagagctt | 360 |
| caggtttggg gtagagacaa caactccctc tcagaagcag gagccgatag acaaggaact | 420 |
| gtatccttta acttccctca gatcactctt tggcagcgac ccctcgtcac aataaagata | 480 |
| gggggggcaat taaggaagc tctattagat acaggagcag atgatacagt attagaagaa | 540 |
| atgaatttgc caggaagatg gaaaccaaaa atgataggg gaattggagg ttttatcaaa | 600 |
| gtaagacagt atgatcagat actcatagaa atctgcggac ataaagctat aggtacagta | 660 |
| ttagtaggac ctacacctgt caacataatt ggaagaaatc tgttgactca gattggctgc | 720 |
| actttaaatt ttcccattag tccaattgaa actgtaccag taaaattaaa gccaggaatg | 780 |
| gattaagagc tc | 792 |

<210> SEQ ID NO 18
<211> LENGTH: 4345
<212> TYPE: DNA
<213> ORGANISM: Artificial Sequence
<220> FEATURE:
<223> OTHER INFORMATION: Description of Artificial Sequence: Synthetic
    HIV-1 Gag -pol sequence

<400> SEQUENCE: 18

| | |
|---|---|
| gcggagtcta gaaggagaga gatgggtgcg agagcgtcgg tattaagcgg gggagaatta | 60 |
| gataaatggg aaaaaattcg gttaaggcca gggggaaaga acaatataaa actaaaacat | 120 |
| atagtatggg caagcaggga gctagaacga ttcgcagtta atcctggcct tttagagaca | 180 |
| tcagaaggct gtagacaaat actgggacag ctacaaccat cccttcagac aggatcagaa | 240 |
| gaacttagat cattatataa tacaatagca gtcctctatt gtgtgcatca aggatagat | 300 |
| gtaaaagaca ccaaggaagc cttagataag atagaggaag agcaaaacaa agtaagaaaa | 360 |
| aaggcacagc aagcagcagc tgacacagga acaacagcc aggtcagcca aaattaccct | 420 |
| atagtgcaga acctccaggg gcaaatggta catcaggcca tatcacctag aactttaaat | 480 |
| gcatgggtaa aagtagtaga agagaaggct ttcagcccag aagtaatacc catgttttca | 540 |

```
gcattatcag aaggagccac cccacaagat ttaaatacca tgctaaacac agtgggggga       600
catcaagcag ccatgcaaat gttaaaagag accatcaatg aggaagctgc agaatgggat       660
agattgcatc cagtgcatgc agggcctatt gcaccaggcc agatgagaga accaagggga       720
agtgacatag caggaactac tagtacccct caggaacaaa taggatggat gacacataat       780
ccacctatcc cagtaggaga atctataaa agatggataa tcctgggatt aaataaaata       840
gtaagaatgt atagccctac cagcattctg gacataagac aaggaccaaa ggaacccttt       900
agagactatg tagaccgatt ctataaaact ctaagagccg agcaagcttc acaagaggta       960
aaaaattgga tgacagaaac cttgttggtc caaaatgcga acccagattg taagactatt      1020
ttaaaagcat tgggaccagg agcgacacta gaagaaatga tgacagcatg tcagggagtg      1080 ggggggacccg gccataaagc aagagttttg gctgaagcaa tgagccaagt aacaaatcca      1140
gctaccataa tgatacagaa aggcaatttt aggaaccaaa gaaagactgt taagtgtttc      1200
aattgtggca agaagggca catagccaaa aattgcaggg cccctaggaa aaagggctgt      1260
tggaaatgtg gaaggaagg acaccaaatg aaagattgta ctgagagaca ggctaatttt      1320
ttagggaaga tctggccttc ccacaaggga aggccaggga attttcttca gagcagacca      1380
gagccaacag ccccaccaga agagagcttc aggtttgggg aagagacaac aactccctct      1440
cagaagcagg agccgataga caaggaactg tatcctttag cttccctcag atcactcttt      1500
ggcagcgacc cctcgtcaca ataaagatag ggggcaatt aaaggaagct ctattagata      1560
caggagcaga tgatacagta ttagaagaaa tgaatttgcc aggaagatgg aaaccaaaaa      1620
tgataggggg aattggaggt tttatcaaag taagacagta tgatcagata ctcatagaaa      1680
tctgcggaca taaagctata ggtacagtat tagtaggacc tacacctgtc aacataattg      1740
gaagaaatct gttgactcag attggctgca ctttaaattt tcccattagt cctattgaga      1800
ctgtaccagt aaaattaaag ccaggaatgg atggcccaaa agttaaacaa tggccattga      1860
cagaagaaaa aataaaagca ttagtagaaa tttgtacaga atggaaaag gaaggaaaaa      1920 tttcaaaaat tgggcctgaa aatccataca atactccagt atttgccata agaaaaaag      1980 acagtactaa atggagaaaa ttagtagatt tcagagaact taataagaga actcaagatt      2040
tctgggaagt tcaattagga ataccacatc ctgcagggtt aaaacagaaa aaatcagtaa      2100
cagtactgga tgtgggcgat gcatattttt cagttccctt agataaagac ttcaggaagt      2160
atactgcatt taccatacct agtataaaca atgagacacc agggattaga tatcagtaca      2220
atgtgcttcc acagggatgg aaaggatcac cagcaatatt ccagtgtagc atgacaaaaa      2280
tcttagagcc ttttagaaaa caaaatccag acatagtcat ctatcaatac atggatgatt      2340
tgtatgtagg atctgactta gaaatagggc agcatagaac aaaaatagag gaactgagac      2400
aacatctgtt gaggtgggga tttaccacac cagacaaaaa acatcagaaa gaacctccat      2460
tcctttggat gggttatgaa ctccatcctg ataaatggac agtacagcct atagtgctgc      2520
cagaaaagga cagctggact gtcaatgaca tacagaaatt agtgggaaaa ttgaattggg      2580
caagtcagat ttatgcaggg attaaagtaa ggcaattatg taaacttctt aggggaacca      2640
aagcactaac agaagtagta ccactaacag aagaagcaga gctagaactg gcagaaaaca      2700
gggagattct aaaagaaccg gtacatggag tgtattatga cccatcaaaa gacttaatag      2760
cagaaataca gaagcagggg caaggccaat ggacatatca aatttatcaa gagccattta      2820
aaaatctgaa aacaggaaaa tatgcaagaa tgaaggtgc ccacactaat gatgtgaaac      2880
aattaacaga ggcagtacaa aaaatagcca cagaaagcat agtaatatgg ggaaagactc      2940
```

```
ctaaatttaa attacccata caaaaggaaa catgggaagc atggtggaca gagtattggc    3000
aagccacctg gattcctgag tgggagtttg tcaataccc tcccttagtg aagttatggt     3060
accagttaga gaaagaaccc ataataggag cagaaacttt ctatgtagat ggggcagcca    3120 ataggaaac taaattagga aaagcaggat atgtaactga cagaggaaga caaaaagttg     3180 tcccctaac ggacacaaca atcagaaga ctgagttaca agcaattcat ctagctttgc      3240
aggattcggg attagaagta aacatagtga cagactcaca atatgcattg gaatcattc     3300 aagcacaacc agataagagt gaatcagagt tagtcagtca ataatagag cagttaataa     3360 aaaggaaaa agtctacctg gcatgggtac cagcacacaa aggaattgga ggaaatgaac     3420
aagtagatgg gttggtcagt gctggaatca ggaaagtact atttttagat ggaatagata    3480
aggcccaaga gaacatgag aaatatcaca gtaattggag agcaatggct agtgatttta    3540
acctaccacc tgtagtagca aaagaaatag tagccagctg tgataaatgt cagctaaaag    3600
gggaagccat gcatggacaa gtagactgta gcccaggaat atggcagcta gattgtacac    3660
atttagaagg aaaagttatc ttggtagcag ttcatgtagc cagtggatat atagaagcag    3720
aagtaattcc agcagagaca gggcaagaaa cagcatactt cctcttaaaa ttagcaggaa    3780
gatggccagt aaaaacagta catacagaca atggcagcaa tttcaccagt actacagtta    3840
aggccgcctg ttggtgggcg gggatcaagc aggaatttgg cattccctac aatccccaaa    3900
gtcaaggagt aatagaatct atgaataaag aattaaagaa aattatagga caggtaagag    3960
atcaggctga acatcttaag acagcagtac aaatggcagt attcatccac aattttaaaa    4020
gaaaaggggg gattgggggg tacagtgcag gggaagaat agtagacata atagcaacag     4080
acatacaaac taaagaatta caaaaacaaa ttacaaaaat tcaaaatttt cgggtttatt    4140
acagggacag cagagatcca gtttggaaag gaccagcaaa gctcctctgg aaaggtgaag    4200
gggcagtagt aatacaagat aatagtgaca taaagtagt gccaagaaga aaagcaaaga    4260
tcatcaggga ttatggaaaa cagatggcag gtgatgattg tgtggcaagt agacaggatg    4320
aggattaaca ctcgagaaag attag                                          4345
```

<210> SEQ ID NO 19
<211> LENGTH: 326
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 3 more nucleic acids

<400> SEQUENCE: 19

```
ggatccttta acatgcctca gatcactctt tggcagcgac ccctcgtcac aataaagata     60 gggggcaat taaggaagc tctattagat acaggagcag atgatacagt attagaagaa      120
atgaatttgc caggaagatg gaaaccaaaa atgataggg gaattggagg ttttatcaaa     180
gtaagacagt atgatcagat actcatagaa atctgcggac ataaagctat aggtacagta    240
ttagtaggac ctacacctgt caacataatt ggaagaaatc tgttgactca gattggctgc    300
actttaaatt ttccctaagc tccaat                                         326
```

<210> SEQ ID NO 20
<211> LENGTH: 329
<212> TYPE: DNA
<213> ORGANISM: Artificial Sequence
<220> FEATURE:

<223> OTHER INFORMATION: Description of Artificial Sequence: Synthetic
      HIV-1 protease sequence with a start codon at position -1 and a
      stop codon after 6 more nucleic acids

<400> SEQUENCE: 20
ggatccttta acatgcctca gatcactctt tggcagcgac ccctcgtcac aataaagata      60 gggggggcaat taaaggaagc tctattagat acaggagcag atgatacagt attagaagaa    120
atgaatttgc caggaagatg gaaaccaaaa atgatagggg gaattggagg ttttatcaaa    180
gtaagacagt atgatcagat actcatagaa atctgcggac ataaagctat aggtacagta    240
ttagtaggac ctacacctgt caacataatt ggaagaaatc tgttgactca gattggctgc    300
actttaaatt ttcccattta agctccaat                                        329

<210> SEQ ID NO 21
<211> LENGTH: 332
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 12 more nucleic acids

<400> SEQUENCE: 21
ggatccttta acatgcctca gatcactctt tggcagcgac ccctcgtcac aataaagata      60 gggggggcaat taaaggaagc tctattagat acaggagcag atgatacagt attagaagaa    120
atgaatttgc caggaagatg gaaaccaaaa atgatagggg gaattggagg ttttatcaaa    180
gtaagacagt atgatcagat actcatagaa atctgcggac ataaagctat aggtacagta    240
ttagtaggac ctacacctgt caacataatt ggaagaaatc tgttgactca gattggctgc    300
actttaaatt ttcccattag ctaagctcca at                                    332

<210> SEQ ID NO 22
<211> LENGTH: 340
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 16 more nucleic acids

<400> SEQUENCE: 22
ggatccttta acatgcctca gatcactctt tggcagcgac ccctcgtcac aataaagata      60 gggggggcaat taaaggaagc tctattagat acaggagcag atgatacagt attagaagaa    120
atgaatttgc caggaagatg gaaaccaaaa atgatagggg gaattggagg ttttatcaaa    180
gtaagacagt atgatcagat actcatagaa atctgcggac ataaagctat aggtacagta    240
ttagtaggac ctacacctgt caacataatt ggaagaaatc tgttgactca gattggctgc    300
actttaaatt ttcccattag tcctaatagg taataggtaa                            340

<210> SEQ ID NO 23
<211> LENGTH: 371
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 51 more nucleic acids

<400> SEQUENCE: 23
ggatccttta acatgcctca gatcactctt tggcagcgac ccctcgtcac aataaagata      60

```
ggggggcaat taaaggaagc tctattagat acaggagcag atgatacagt attagaagaa      120
atgaatttgc caggaagatg gaaaccaaaa atgataggg gaattggagg ttttatcaaa      180
gtaagacagt atgatcagat actcatagaa atctgcggac ataaagctat aggtacagta      240
ttagtaggac ctacacctgt caacataatt ggaagaaatc tgttgactca gattggctgc      300
actttaaatt ttcccattag tccaattgaa actgtaccag taaaattaaa gccaggaatg      360
gattaagagc t                                                          371
```

<210> SEQ ID NO 24
<211> LENGTH: 388
<212> TYPE: DNA
<213> ORGANISM: Artificial Sequence
<220> FEATURE:
<223> OTHER INFORMATION: Description of Artificial Sequence: Synthetic
     HIV-1 protease sequence with a start codon at position -1 and a
     stop codon after 66 more nucleic acids

<400> SEQUENCE: 24

```
ggatcctta acatgcctca gatcactctt tggcagcgac ccctcgtcac aataaagata      60
ggggggcaat taaggaagc tctattagat acaggagcag atgatacagt attagaagaa      120
atgaatttgc caggaagatg gaaaccaaaa atgataggg gaattggagg ttttatcaaa      180
gtaagacagt atgatcagat actcatagaa atctgcggac ataaagctat aggtacagta      240
ttagtaggac ctacacctgt caacataatt ggaagaaatc tgttgactca gattggctgc      300
actttaaatt ttcccattag tcctattgag actgtaccag taaaattaaa gccaggaatg      360
gatggcccaa aagttaaata ataggtaa                                        388
```

<210> SEQ ID NO 25
<211> LENGTH: 477
<212> TYPE: DNA
<213> ORGANISM: Artificial Sequence
<220> FEATURE:
<223> OTHER INFORMATION: Description of Artificial Sequence: Synthetic
     HIV-1 protease sequence with a start codon at position -1 and a
     stop codon after 156 more nucleic acids

<400> SEQUENCE: 25

```
ggatcctta acatgcctca gatcactctt tggcagcgac ccctcgtcac aataaagata      60
ggggggcaat taaggaagc tctattagat acaggagcag atgatacagt attagaagaa      120
atgaatttgc caggaagatg gaaaccaaaa atgataggg gaattggagg ttttatcaaa      180
gtaagacagt atgatcagat actcatagaa atctgcggac ataaagctat aggtacagta      240
ttagtaggac ctacacctgt caacataatt ggaagaaatc tgttgactca gattggctgc      300
actttaaatt ttcccattag tcctattgag actgtaccag taaaattaaa gccaggaatg      360
gatggcccaa aagttaaaca atggccattg acagaagaaa aaataaaagc attagtagaa      420
atttgtacag aaatggaaaa ggaaggaaaa atttcaaaaa ttgggcctaa taggtaa        477
```

<210> SEQ ID NO 26
<211> LENGTH: 669
<212> TYPE: DNA
<213> ORGANISM: Artificial Sequence
<220> FEATURE:
<223> OTHER INFORMATION: Description of Artificial Sequence: Synthetic
     HIV-1 protease sequence with a start codon at position -1 and a
     stop codon after 342 more nucleic acids

<400> SEQUENCE: 26

```
ggatccttta acatgcctca gatcactctt tggcagcgac ccctcgtcac aataaagata    60 gggggcaat  taaggaagc  tctattagat  acaggagcag  atgatacagt  attagaagaa   120
atgaatttgc caggaagatg gaaaccaaaa atgatagggg gaattggagg ttttatcaaa   180
gtaagacagt atgatcagat actcatagaa atctgcggac ataaagctat aggtacagta   240
ttagtaggac ctacacctgt caacataatt ggaagaaatc tgttgactca gattggctgc   300
actttaaatt tttcctatta gtcctattga gactgtacca gtaaaattaa agccaggaat   360
ggatggccca aaagttaaac aatggccatt gacagaagaa aaaataaaag cattagtaga   420
aatttgtaca gaaatggaaa aggaaggaaa aatttcaaaa attgggcctg aaaatccata   480
caatactcca gtatttgcca taagaaaaaa agacagtact aaatggagaa aattagtaga   540
tttcagagaa cttaataaga gaactcaaga tttctgggaa gttcaattag gaataccaca   600
tcctgcaggg ttaaaacaga aaaaatcagt aacagtactg gatgtgggcg atgctaatag   660
gtaataggt                                                            669

<210> SEQ ID NO 27
<211> LENGTH: 796
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 471 more nucleic acids

<400> SEQUENCE: 27
ggatccttta acatgcctca gatcactctt tggcagcgac ccctcgtcac aataaagata    60 gggggcaat  taaggaagc  tctattagat  acaggagcag  atgatacagt  attagaagaa   120
atgaatttgc caggaagatg gaaaccaaaa atgatagggg gaattggagg ttttatcaaa   180
gtaagacagt atgatcagat actcatagaa atctgcggac ataaagctat aggtacagta   240
ttagtaggac ctacacctgt caacataatt ggaagaaatc tgttgactca gattggctgc   300
actttaaatt ttcccattag tcctattgag actgtaccag taaaattaaa gccaggaatg   360
gatggcccaa aagttaaaca atggccattg acatgaagaa aaaataaaag cattagtaga   420
aatttgtaca gaaatggaaa aggaaggaaa aatttcaaaa attgggcctg aaaatccata   480
caatactcca gtatttgcca taagaaaaaa agacagtact aaatggagaa aattagtaga   540
tttcagagaa cttaataaga gaactcaaga tttctgggaa gttcaattag gaataccaca   600
tcctgcaggg ttaaaacaga aaaaatcagt aacagtactg gatgtgggcg atgcatattt   660
ttcagttccc ttagataaag acttcaggaa gtatactgca tttaccatac ctagtataaa   720
caatgagaca ccagggatta gatatcagta caatgtgctt ccacagggat ggaaaggatc   780
actaataggt aatagg                                                    796

<210> SEQ ID NO 28
<211> LENGTH: 922
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 591 more nucleic acids

<400> SEQUENCE: 28
ggatccttta acatgcctca gatcactctt tggcagcgac ccctcgtcac aataaagata    60 gggggcaat  taaggaagc  tctattagat  acaggagcag  atgatacagt  attagaagaa   120
```

```
atgaatttgc caggaagatg gaaaccaaaa atgatagggg gaattggagg ttttatcaaa      180
gtaagacagt atgatcagat actcatagaa atctgcggac ataaagctat aggtacagta      240
ttagtaggac ctacacctgt caacataatt ggaagaaatc tgttgactca gattggctgc      300
actttaaatt ttcccattag tcctattgag actgtaccag taaaattaaa gccaggaatg      360
gatggcccaa agttaaaca atggccattg acagaagaaa aaataaaagc attagtagaa       420
atttgtacag aaatggaaaa ggaaggaaaa atttcaaaaa ttgggcctga aaatccatac      480
aatactccag tatttgccat aagaaaaaa gacagtacta aatggagaaa attagtagat      540
ttcagagaac ttaataagag aactcaagat ttctgggaag ktcaattarg aataccacat      600
cctgcagggt taaaacagaa aaaatcagta acagtactgg atgtgggcga tgcatatttt     660
tcagttccct tagataaaga cttcaggaag tatactgcat ttaccatacc tagtataaac      720
aatgagacac cagggattag atatcagtac aatgtgcttc cacagggatg gaaaggatca     780
ccagcaatat tccagtgtag catgacaaaa atcttagagc cttttagaaa acaaaatcca     840
gacatagtca tctatcaata catggatgat ttgtatgtag gatctgactt agaaataggg     900
ctaataggta ataggtaaga gc                                                922
```

<210> SEQ ID NO 29
<211> LENGTH: 994
<212> TYPE: DNA
<213> ORGANISM: Artificial Sequence
<220> FEATURE:
<223> OTHER INFORMATION: Description of Artificial Sequence: Synthetic HIV-1 protease sequence with a start codon at position -1 and a stop codon after 663 more nucleic acids

<400> SEQUENCE: 29

```
ggatccttta acatgcctca gatcactctt tggcagcgac ccctcgtcac aataaagata      60 gggggggcaat taaaggaagc tctattagat acaggagcag atgatacagt attagaagaa    120
atgaatttgc caggaagatg gaaaccaaaa atgatagggg gaattggagg ttttatcaaa     180
gtaagacagt atgatcagat actcatagaa atctgcggac ataaagctat aggtacagta     240
ttagtaggac ctacacctgt caacataatt ggaagaaatc tgttgactca gattggctgc     300
actttaaatt ttcccattag tcctattgag actgtaccag taaaattaaa gccaggaatg     360
gatggcccaa agttaaaca atggccattg acagaagaaa aaataaaagc attagtagaa      420
atttgtacag aaatggaaaa ggaaggaaaa atttcaaaaa ttgggcctga aaatccatac     480
aatactccag tatttgccat aagaaaaaa gacagtacta aatggagaaa attagtagat     540
ttcagagaac ttaataagag aactcaagat ttctgggaag ttcaattagg aataccacat     600
cctgcagggt taaaacagaa aaaatcagta acagtactgg atgtgggcga tgcatatttt    660
tcagttccct tagataaaga cttcaggaag tatactgcat ttaccatacc tagtataaac     720
aatgagacac cagggattag atatcagtac aatgtgcttc cacagggatg gaaaggatca    780
ccagcaatat tccagtgtag catgacaaaa atcttagagc cttttagaaa acaaaatcca    840
gacatagtca tctatcaata catggatgat ttgtatgtag gatctgactt agaaataggg    900
cagcatagaa caaaaataga ggaactgrga caacatctgt tgaggtgggg atttaccaca    960
ccagacaaaa aactaatagg taataggtaa gagc                                  994
```

<210> SEQ ID NO 30
<211> LENGTH: 1002
<212> TYPE: DNA

<213> ORGANISM: Artificial Sequence
<220> FEATURE:
<223> OTHER INFORMATION: Description of Artificial Sequence: Synthetic HIV-1 protease sequence with a start codon at position -1 and a stop codon after 675 more nucleic acids

<400> SEQUENCE: 30

```
ggatccttta acatgcctca gatcactctt tggcagcgac ccctcgtcac aataaagata      60
ggggggcaat taaggaagc tctattagat acaggagcag atgatacagt attagaagaa       120
atgaatttgc caggaagatg gaaaccaaaa atgatagggg gaattggagg ttttatcaaa     180
gtaagacagt atgatcagat actcatagaa atctgcggac ataaagctat aggtacagta    240
ttagtaggac ctacacctgt caacataatt ggaagaaatc tgttgactca gattggctgc   300
actttaaatt ttcccattag tcctattgag actgtaccag twaaattaaa gccaggaatg   360
gatggcccaa aagttaaaca atggccattg acagaagaaa aaataaaagc attagtagaa    420
atttgtacag aaatggaaaa ggaaggaaaa atttcaaaaa ttgggcctga aaatccatac   480
aatactccag tatttgccat aaagaaaaaa gacagtacta aatggagaaa attagtagat    540
ttcagagaac ttaataagag aactcaagat ttctgggaag ttcaattagg aataccacat     600
cctgcagggt taaaacagaa aaaatcagta acagtactgg atgtgggcga tgcatatttt    660
tcagttccct tagataaaga cttcaggaag tatactgcat ttaccatacc tagtataaac     720
aatgagacac cagggattag atatcagtac aatgtgcttc cacagggatg aaaggatca     780
ccagcaatat tccagtgtag catgacaaaa atcttagagc cttttagaaa acaaaatcca   840
gacatagtca tctatcaata catggatgat ttgtatgtag gatctgactt agaaataggg  900
cagcatagaa caaaaataga ggaactgaga caacatctgt tgaggtgggg atttaccaca    960
ccagacaaaa aacatcagaa agaacctaat aggtaatagg ta                              1002
```

<210> SEQ ID NO 31
<211> LENGTH: 1005
<212> TYPE: DNA
<213> ORGANISM: Artificial Sequence
<220> FEATURE:
<223> OTHER INFORMATION: Description of Artificial Sequence: Synthetic HIV-1 protease sequence with a start codon at position -1 and a stop codon after 678 more nucleic acids

<400> SEQUENCE: 31

```
ggatccttta acatgcctca gatcactctt tggcagcgac ccctcgtcac aataaagata      60
ggggggcaat taaggaagc tctattagat acaggagcag atgatacagt attagaagaa      120
atgaatttgc caggaagatg gaaaccaaaa atgatagggg gaattggagg ttttatcaaa    180
gtaagacagt atgatcagat actcatagaa atctgcggac ataaagctat aggtacagta   240
ttagtaggac ctacacctgt caacataatt ggaagaaatc tgttgactca gattggctgc   300
actttaaatt ttcmcattat tcctattgas actgtaccag tcaaattaaa gccmggagtg   360
gatggcccaa aagttaaaca atggccattg acagaagaaa aaataaaagc attagtagaa    420
atttgtacag aaatggaaaa ggaaggaaaa atttcaaaaa ttgggcctga aaatccatac   480
aatactccag tatttgccat aaagaaaaaa gacagtacta aatggagaaa attagtagat    540
ttcagagaac ttaataagag aactcaagat ttctgggaag ttcaattagg aataccacat     600
cctgcagggt taaaacagaa aaaatcagta acagtactgg atgtgggcga tgcatatttt    660
tcagttccct tagataaaga cttcaggaag tatactgcat ttaccatacc tagtataaac     720
aatgagacac cagggattag atatcagtac aatgtgcttc cacagggatg aaaggatca     780
```

```
ccagcaatat tccagtgtag catgacaaaa atcttagagc cttttagaaa acaaaatcca      840
gacatagtca tctatcaata catggatgat ttgtatgtag gatctgactt agaaataggg      900
cagcatagaa caaaaataga ggaactgaga caacatctgt tgaggtgggg atttaccaca      960
ccagacaaaa aacatcagaa agaacctcct aataggtaat aggta                    1005
```

<210> SEQ ID NO 32
<211> LENGTH: 1015
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 684 more nucleic acids

<400> SEQUENCE: 32

```
ggatccttta acatgcctca gatcactctt tggcagcgac ccctcgtcac aataaagata       60 gggggggcaat taaggaagc tctattagat acaggagcag atgatacagt attagaagaa      120
atgaatttgc caggaagatg gaaaccaaaa atgatagggg gaattggagg ttttatcaaa      180
gtaagacagt atgatcagat actcatagaa atctgcggac ataaagctat aggtacagta      240
ttagtaggac ctacacctgt caacataatt ggaagaaatc tgttgactca gattggctgc      300
actttaaatt ttcccattag tcctattgag actgtaccag taaaattaaa gccaggaatg      360
gatggcccaa aagttaaaca atggccattg acagaagaaa aaataaaagc attagtagaa      420
atttgtacag aaatggaaaa ggaaggaaaa atttcaaaaa ttgggcctga aaatccatac      480
aatactccag tatttgccat aaagaaaaaa gacagtacta aatggagaaa attagtagat      540
ttcagagaac ttaataagag aactcaagat ttctgggaag ttcaattagg aataccacat      600
cctgcagggt taaaacagaa aaaatcagta acagtactgg atgtgggcga tgcatatttt      660
tcagttccct tagataaaga cttcaggaag tatactgcat ttaccatacc tagtataaac      720
aatgagacac cagggattag atatcagtac aatgtgcttc cacagggatg gaaaggatca      780
ccagcaatat tccagtgtag catgacaaaa atcttagagc cttttagaaa acaaaatcca      840
gacatagtca tctatcaata catggatgat ttgtatgtag gatctgactt agaaataggg      900
cagcatagaa caaaaataga ggractgaga caacatctgt tgaggtgggg atttaccaca      960
ccagacaaaa aacatcagaa agaacctcca ttcctaatag gtaataggta agagc         1015
```

<210> SEQ ID NO 33
<211> LENGTH: 1257
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 939 more nucleic acids

<400> SEQUENCE: 33

```
ggatccttta acatgcctca gatcactctt tggcagcgac ccctcgtcac aataaagata       60 gggggggcaat taaggaagc tctattagat acaggagcag atgatacagt attagaagaa      120
atgaatttgc caggaagatg gaaaccaaaa atgatagggg gaattggagg ttttatcaaa      180
gtaagacagt atgatcagat actcatagaa atctgcggac ataaagctat aggtacagta      240
ttagtaggac ctacacctgt caacataatt ggaagaaatc tgttgactca gattggctgc      300
actttaaatt ttcccattag tcctattgag actgtaccag taaaattaaa gccaggaatg      360
```

```
gatggcccaa aagttaaaca atggccattg acagaagaaa aaataaaagc attagtagaa      420
atttgtacag aaatggaaaa ggaaggaaaa atttcaaaaa ttgggcctga aaatccatac      480
aatactccag tatttgccat aaagaaaaaa gacagtacta aatggagaaa attagtagat      540
ttcagagaac ttaataagag aactcaagat ttctgggaag ttcaattagg aataccacat      600
cctgcagggt taaaacagaa aaaatcagta acagtactgg atgtgggcga tgcatatttt      660
tcagttccct tagataaaga cttcaggaag tatactgcat ttaccatacc tagtataaac      720
aatgagacac cagggattag atatcagtac aatgtgcttc cacagggatg aaaggatca      780 ccagcaatat tccagtgtag catgacaaaa atcttagagc cttttagaaa acaaaatcca      840
gacatagtca tctatcaata catggatgat ttgtatgtag gatctgactt agaaataggg      900
cagcatagaa caaaaataga ggaactgaga caacatctgt tgaggtgggg atttaccaca      960
ccagacaaaa aacatcagaa agaacctcca ttcctttgga tgggttatga actccatcct     1020
gataaatgga cagtacagcc tatagtgctg ccagaaaagg acagctggac tgtcaatgac     1080
atacagaaat tagtgggaaa attgaattgg gcaagtcaga tttatgcagg gattaaagta     1140
aggcaattat gtaaacttct taggggaacc aaagcactaa cagragtagt accactaaca     1200
gaagaagcag agctagaact ggcagaaaac agggagattc taaagaacc taatagg        1257

<210> SEQ ID NO 34
<211> LENGTH: 1369
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 1044 more nucleic acids

<400> SEQUENCE: 34
ggatccttta acatgcctca gatcactctt tggcagcgac ccctcgtcac aataaagata       60
ggggggcaat taaggaagc tctattagat acagagcag atgatacagt attagaagaa      120
atgaatttgc caggaagatg gaaaccaaaa atgataggg gaattggagg ttttatcaaa      180
gtaagacagt atgatcagat actcatagaa atctgcggac ataaagctat aggtacagta      240
ttagtaggac ctacacctgt caacataatt ggaagaaatc tgttgactca gattggctgc      300
actttaaatt ttcccattag tcctattgag actgtaccag taaaattaaa gccaggaatg      360
gatggcccaa aagttaaaca atggccattg acagaagaaa aaataaaagc attagtagaa      420
atttgtacag aaatggaaaa ggaaggaaaa atttcaaaaa ttgggcctga aaatccatac      480
aatactccag tatttgccat aaagaaaaaa gacagtacta aatggagaaa attagtagat      540
ttcagagaac ttaataagag aactcaagat ttctgggaag ttcaattagg aataccacat      600
cctgcagggt taaaacagaa aaaatcagta acagtactgg atgtgggcga tgcatatttt      660
tcagttycct tagataaaga cttcaggaag tatactgcat ttaccatacc tagtataaac      720
aatgagacac cagggattag atatcagtac aatgtgcttc cacagggatg aaaggatca      780 ccagcaatat tccagtgtag catgacaaaa atcttagagc cttttagaaa acaaaatcca      840
gacatagtca tctatcaata catggatgat ttgtatgtag gatctgactt agaaataggg      900
cagcatagaa caaaaataga ggaactgaga caacatctgt tgaggtgggg atttaccaca      960
ccagacaaaa aacatcagaa agaacctcca ttcctttgga tgggttatga actccatcct     1020
gataaatgga cagtacagcc tatagtgctg ccagaaaagg acagctggac tgtcaatgac     1080
atacagaaat tagtgggaaa attgaattgg gcaagtcaga tttatgcagg gattaaagta     1140
```

-continued

```
aggcaattat gtaaacttct taggggaacc aaagcactaa cagaagtagt accactaaca    1200
gaagaagcag agctagaact ggcagaaaac agggagattc taaagaacc ggtacatgga     1260 gtgtattatg acccatcaaa agacttaata gcagaaatac agaagcaggg gcaaggccaa    1320
tggacatatc aaatttatca agagccatta aaaatctaat aggtaatag                1369
```

<210> SEQ ID NO 35
<211> LENGTH: 1405
<212> TYPE: DNA
<213> ORGANISM: Artificial Sequence
<220> FEATURE:
<223> OTHER INFORMATION: Description of Artificial Sequence: Synthetic
HIV-1 protease sequence with a start codon at position -1 and a
stop codon after 1083 more nucleic acids

<400> SEQUENCE: 35

```
ggatccttta acatgcctca gatcactctt tggcagcgac ccctcgtcac aataaagata     60 gggggggcaat taaggaagc tctattagat acaggagcag atgatacagt attagaagaa    120
atgaatttgc caggaagatg gaaaccaaaa atgataggg gaattggagg tttatcaaa      180 gtaagacagt atgatcagat actcatagaa atctgcggac ataaagctat aggtacagta    240
ttagtaggac ctacacctgt caacataatt ggaagaaatc tgttgactca gattggctgc    300
actttaaatt ttcccattag tcctattgag actgtaccag taaaattaaa gccaggaatg    360
gatggcccaa aagttaaaca atggccattg acagaagaaa aaataaaagc attagtagaa    420
atttgtacag aaatggaaaa ggaaggaaaa atttcaaaaa ttgggcctga aaatccatac    480
aatactccag tatttgccat aaagaaaaaa gacagtacta aatggagaaa attagtagat    540
ttcagagaac ttaataagag aactcaagat ttctgggaag ttcaattagg aataccacat    600
cctgcagggt taaaacagaa aaaatcagta acagtactgg atgtgggcga tgcatatttt    660
tcagttycct tagataaaga cttcaggaag tatactgcat ttaccatacc tagtataaac    720
aatgagacac cagggattag atatcagtac aatgtgcttc cacagggatg aaaggatca    780 ccagcaatat tccagtgtag catgacaaaa atcttagagc cttttagaaa acaaaatcca    840
gacatagtca tctatcaata catggatgat ttgtatgtag gatctgactt agaaataggg    900
cagcatagaa caaaaataga ggaactgaga caacatctgt tgaggtgggg atttaccaca    960
ccagacaaaa aacatcagaa agaacctcca ttcctttgga tgggttatga actccatcct    1020
gataaatgga cagtacagcc tatagtgctg ccagaaaagg acagctggac tgtcaatgac    1080
atacagaaat tagtgggaaa attgaattgg gcaagtcaga tttatgcagg gattaaagta    1140
aggcaattat gtaaacttct taggggaacc aaagcactaa cagaagtagt accactaaca    1200
gaagaagcag agctagaact ggcagaaaac agggagattc taaagaacc ggtacatgga     1260 gtgtattatg acccatcaaa agacttaata gcagaaatac agaagcaggg gcaaggccaa    1320
tggacatatc aaatttatca agagccatta aaaatctgaa acaggaaag tatgcaagaa    1380 tgaagggtgc cmtaataggt aatag                                          1405
```

<210> SEQ ID NO 36
<211> LENGTH: 2851
<212> TYPE: DNA
<213> ORGANISM: Artificial Sequence
<220> FEATURE:
<223> OTHER INFORMATION: Description of Artificial Sequence: Synthetic
HIV-1 protease sequence with a start codon at position -1 and a
stop codon after 2511 more nucleic acids

<400> SEQUENCE: 36

```
ggatccttta acatgcctca gatcactctt tggcagcgac ccctcgtcac aataaagata     60
gggggggcaat taaaggaagc tctattagat acaggagcag atgatacagt attagaagaa    120
atgaatttgc caggaagatg gaaaccaaaa atgatagggg gaattggagg ttttatcaaa    180
gtaagacagt atgatcagat actcatagaa atctgcggac ataaagctat aggtacagta    240
ttagtaggac ctacacctgt caacataatt ggaagaaatc tgttgactca gattggctgc    300
actttaaatt ttcccattag tcctattgag actgtaccag taaaattaaa gccaggaatg    360
gatggcccaa aagttaaaca atggccattg acagaagaaa aaataaaagc attagtcgaa    420
atttgtacag aaatggaaaa ggaaggaaaa atttcaaaaa ttgggcctga aaatccatac    480
aatactccag tatttgccat aaagaaaaaa gacagtacta atggagaaaa attagtagat    540
ttcagagaac ttaataagag aactcaagat ttctgggaag ttcaattagg aataccacat    600
cctgcagggt taaaacagaa aaaatcagta acagtactgg atgtgggcga tgcatatttt    660
tcagttccct tagataaaga cttcaggaag tatactgcat ttaccatacc tagtataaac    720
aatgagacac cagggattag atatcagtac aatgtgcttc cacagggatg aaaggatca    780
ccagcaatat tccagtgtag catgacaaaa atcttagagc cttttagaaa acaaaatcca    840
gacatagtca tctatcaata catggatgat ttgtatgtag gatctgactt agaaataggg    900
cagcatagaa caaaaataga ggaactgaga caacatctgt tgaggtgggg atttaccaca    960
ccagacaaaa aacatcagaa agaacctcca ttcctttgga tgggttatga actccatcct   1020
gataaatgga cagtacagcc tatagtgctg ccagaaaagg acagctggac tgtcaatgac   1080
atacagaaat tagtgggaaa attgaattgg gcaagtcaga tttatgcagg gattaaagta   1140
aggcaattat gtaaacttct taggggaacc aaagcactaa cagaagtagt accactaaca   1200
gaagaagcag agctagaact ggcagaaaac agggagattc taaaagaacc ggtacatgga   1260
gtgtattatg acccatcaaa agacttaata gcagaaatac agaagcaggg gcaaggccaa   1320
tggacatatc aaatttatca agagccattt aaaaatctga aaacaggaaa gtatgcaaga   1380
atgaaggtg cccacactaa tgatgtgaaa caattaacag aggcagtaca aaaaatagcc   1440
acagaaagca tagtaatatg gggaaagact cctaaattta attacccat acaaaaggaa   1500
acatgggaag catggtggac agagtattgg caagccacct ggattcctga gtgggagttt   1560
gtcaataccc ctcccttagt gaagttatgg taccagttag agaaagaacc cataatagga   1620
gcagaaactt tctatgtaga tggggcagcc aatagggaaa ctaaattagg aaaagcagga   1680
tatgtaactg acagaggaag acaaaaagtt gtccccctaa cggacacaac aaatcagaag   1740
actgagttac aagcaattca tctagctttg caggattcgg gattagaagt aaacatagtg   1800
acagactcac aatatgcatt gggaatcatt caagcacaac cagataagag tgaatcagag   1860
ttagtcagtc aaataataga gcagttaata aaaaaggaaa aagtctacct ggcatgggta   1920
ccagcacaca aaggaattgg aggaaatgaa caagtagata aattggtcag tgctggaatc   1980
aggaaagtac tatttttaga tggaatagat aaggcccaag aagaacatga gaaatatcac   2040
agtaattgga gagcaatggc tagtgatttt aacctaccac ctgtagtagc aaaagaaata   2100
gtagccagct gtgataaatg tcagctaaaa ggggaagcca tgcatggaca agtagactgt   2160
agcccaggaa tatggcagct agattgtaca catttagaag gaaagttat cttggtagca   2220
gttcatgtag ccagtggata tatagaagca gaagtaattc cagcagagac agggcaagaa   2280
acagcatact cctcttaaaa attagcagga agatggccag taaaaacagt acatacagac   2340
```

```
aatggcagca atttcaccag tactacagtt aaggccgcct gttggtgggc ggggatcaag    2400
caggaatttg gcattcccta caatccccaa agtcaaggag taatagaatc tatgaataaa    2460
gaattaaaga aaattatagg acaggtaaga gatcaggctg aacatcttaa gacagcagta    2520
caaatggcag tattcatcca caattttaaa agaaaagggg ggattggggg gtacagtgca    2580
ggggaaagaa tagtagacat aatagcaaca gacatacaaa ctaaagaatt acaaaaacaa    2640
attacaaaaa ttcaaaattt tcgggtttat tacagggaca gcagagatcc agtttggaaa    2700
ggaccagcaa agctcctctg gaaaggtgaa ggggcagtag taatacaaga taatagtgac    2760
ataaaagtag tgccaagaag aaaagcaaag atcatcaggg attatggaaa acagatggca    2820
ggtgagattg tggcaagta gacaggatta g                                    2851
```

<210> SEQ ID NO 37
<211> LENGTH: 2876
<212> TYPE: DNA
<213> ORGANISM: Artificial Sequence
<220> FEATURE:
<223> OTHER INFORMATION: Description of Artificial Sequence: Synthetic
      HIV-1 protease sequence with a start codon at position -1 and a
      stop codon after 2544 more nucleic acids

<400> SEQUENCE: 37

```
ggatccttta acatgcctca gatcactctt tggcagcgac ccctcgtcac aataaagata      60 gggggggcaat taaaggaagc tctattagat acaggagcag atgatacagt attagaagaa     120
atgaatttgc caggaagatg gaaaccaaaa atgatagggg gaattggagg ttttatcaaa     180
gtaagacagt atgatcagat actcatagaa atctgcggac ataaagctat aggtacagta     240
ttagtaggac ctacacctgt caacataatt ggaagaaatc tgttgactca gattggctgc     300
actttaaatt ttcccattag tcctattgag actgtaccag taaaattaaa gccaggaatg     360
gatggcccaa aagttaaaca atggccattg acagaagaaa aaataaaagc attagtagaa     420
atttgtacag aaatggaaaa ggaaggaaaa atttcaaaaa ttgggcctga aaatccatac     480
aatactccag tatttgccat aaagaaaaaa gacagtacta atggagaaaa attagtagat     540
ttcagagaac ttaataagag aactcaagat ttctgggaag ttcaattagg aataccacat     600
cctgcagggt taaaacagaa aaaatcagta acagtactgg atgtgggcga tgcatatttt     660
tcagttccct tagataaaga cttcaggaag tatactgcat ttaccatacc tagtataaac     720
aatgagacac cagggattag atatcagtac aatgtgcttc cacagggatg gaaaggatca     780
ccagcaatat tccagtgtag catgacaaaa atcttagagc cttttagaaa acaaaatcca     840
gacatagtca tctatcaata catggatgat ttgtatgtag gatctgactt agaaataggg     900
cagcatagaa caaaaataga ggaactgaga caacatctgt tgaggtgggg atttaccaca     960
ccagacaaaa aacatcagaa agaacctcca ttcctttgga tgggttatga actccatcct    1020
gataaatgga cagtacagcc tatagtgctg ccagaaaagg acagctggac tgtcaatgac    1080
atacagaaat tagtgggaaa attgaattgg gcaagtcaga tttatgcagg gattaaagta    1140
aggcaattat gtaaacttct taggggaacc aaagcactaa cagaagtagt accactaaca    1200
gaagaagcag agctagaact ggcagaaaac agggagattc taaaagaacc ggtacatgga    1260
gtgtattatg acccatcaaa agacttaata gcagaaatac agaagcaggg gcaaggccaa    1320
tggacatatc aaatttatca agagccattt aaaaatctga aaacaggaaa atatgcaaga    1380
atgaagggtg cccacactaa tgatgtgaaa caattaacag aggcagtaca aaaaatagcc    1440
```

```
acagaaagca tagtaatatg gggaaagact cctaaattta aattacccat acaaaggaa    1500 acatgggaag catggtggac agagtattgg caagccacct ggattcctga gtgggagttt    1560
gtcaataccc ctcccttagt gaagttatgg taccagttag agaaagaacc cataatagga    1620
gcagaaactt tctatgtaga tggggcagcc aatagggaaa ctaaattagg aaaagcagga    1680
tatgtaactg acagaggaag acaaaaagtt gtcccctaa cggacacaac aaatcagaag    1740
actgagttac aagcaattca tctagctttg caggattcgg gattagaagt aaacatagtg    1800
acagactcac aatatgcatt gggaatcatt caagcacaac cagataagag tgaatcagag    1860
ttagtcagtc aaataataga gcagttaata aaaaaggaaa aagtctacct ggcatgggta    1920
ccagcacaca aaggaattgg aggaaatgaa caagtagatg ggttggtcag tgctggaatc    1980
aggaaagtac tatttttaga tggaatagat aaggcccaag aagaacatga gaaatatcac    2040
agtaattgga gagcaatggc tagtgatttt aacctaccac ctgtagtagc aaaagaaata    2100
gtagccagct gtgataaatg tcagctaaaa ggggaagcca tgcatggaca agtagactgt    2160
agcccaggaa tatggcagct agattgtaca catttagaag gaaaagttat cttggtagca    2220
gttcatgtag ccagtggata tatagaagca gaagtaattc cagcagagac agggcaagaa    2280
acagcatact tcctcttaaa attagcagga agatggccag taaaaacagt acatacagac    2340
aatggcagca atttcaccag tactacagtt aaggccgcct gttggtgggc ggggatcaag    2400
caggaatttg gcattcccta caatccccaa agtcaaggag taatagaatc tatgaataaa    2460
gaattaaaga aaattatagg acaggtaaga gatcaggctg aacatcttaa gacagcagta    2520
caaatggcag tattcatcca caattttaaa agaaaagggg ggattggggg gtacagtgca    2580
ggggaaagaa tagtagacat aatagcaaca gacatacaaa ctaaagaatt acaaaaacaa    2640
attacaaaaa ttcaaaattt tcgggtttat tacagggaca gcagagatcc agtttggaaa    2700
ggaccagcaa agctcctctg gaaaggtgaa ggggcagtag taatacaaga taatagtgac    2760
ataaaagtag tgccaagaag aaaagcaaag atcatcaggg attatggaaa acagatggca    2820
ggtgatgatt gtgtggcaag tagacaggat gaggattaac actcgagaaa gattag      2876
```

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      FgagPol oligonucleotide

<400> SEQUENCE: 38
gcggagtcta gaaggagaga gatgggtgcg aga                                  33

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      RGagPol oligonucleotide

<400> SEQUENCE: 39
ctaatctttc tcgagtgtta atcctcatcc tgtctacttg                           40

<210> SEQ ID NO 40
<211> LENGTH: 18
<212> TYPE: DNA
<213> ORGANISM: Artificial Sequence

```
<220> FEATURE:
<223> OTHER INFORMATION: Description of Artificial Sequence: Synthetic
      5' Gal primer

<400> SEQUENCE: 40
tgaataacca ctttaact                                                   18

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      3' RP-12 primer

<400> SEQUENCE: 41
cattcctggc tttaatttta ctggtacagt ctcaataggg ctaatttaaa aatttaaagt     60

<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence: Synthetic
      5' F3 primer

<400> SEQUENCE: 42
tatactttaa cgtcaaggag aaaaaacccc ggatccttta acatgcctca gatc           54

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      3' M13F primer

<400> SEQUENCE: 43
gttttcccag tcaccacg                                                   18

<210> SEQ ID NO 44
<211> LENGTH: 53
<212> TYPE: DNA
<213> ORGANISM: Artificial Sequence
<220> FEATURE:
<223> OTHER INFORMATION: Description of Artificial Sequence: Synthetic
      sense Gal-gp-rh sequence

<400> SEQUENCE: 44
tatactttaa cgtcaaggag aaaaaacccc ggatccatgt acgatgtacg atg            53

<210> SEQ ID NO 45
<211> LENGTH: 53
<212> TYPE: DNA
<213> ORGANISM: Artificial Sequence
<220> FEATURE:
<223> OTHER INFORMATION: Description of Artificial Sequence: Synthetic
      antisense Gal-gp-rh sequence

<400> SEQUENCE: 45
atatgaaatt gcagttcctc ttttttgggg cctaggtaca tgctacatgc tac            53

<210> SEQ ID NO 46
<211> LENGTH: 54
<212> TYPE: DNA
<213> ORGANISM: Artificial Sequence
<220> FEATURE:
```

<223> OTHER INFORMATION: Description of Artificial Sequence: Synthetic
      sense M13-gp-rh sequence

<400> SEQUENCE: 46
taataggtaa taggtaagag ctccaattcg ccctatagtg agtcgtatta caat        54

<210> SEQ ID NO 47
<211> LENGTH: 54
<212> TYPE: DNA
<213> ORGANISM: Artificial Sequence
<220> FEATURE:
<223> OTHER INFORMATION: Description of Artificial Sequence: Synthetic
      antisense M13-gp-rh sequence

<400> SEQUENCE: 47
attatccatt atccattctc gaggttaagc gggatatcac tcagcataat gtta        54

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      F1071-120B primer

<400> SEQUENCE: 48
gagggatcca tgtggggtag agacaacaac tcc        33

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      5'-a435 primer

<400> SEQUENCE: 49
caggctaatt ttttaaggg        19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      R-a435 primer

<400> SEQUENCE: 50
cccttaaaaa attagcctg        19

<210> SEQ ID NO 51
<211> LENGTH: 60
<212> TYPE: DNA
<213> ORGANISM: Artificial Sequence
<220> FEATURE:
<223> OTHER INFORMATION: Description of Artificial Sequence: Synthetic
      F1071B1 primer

<400> SEQUENCE: 51
ggatccatga tgacagcatg tcagggagtg ggaggacccg gccataaggc aagagttttg        60

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic 5' GP7 primer

<400> SEQUENCE: 52
atgatgacag catgtgaggg ag    22

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      3' R772 primer

<400> SEQUENCE: 53
cctgaaaatc catayaayac    20

<210> SEQ ID NO 54
<211> LENGTH: 59
<212> TYPE: DNA
<213> ORGANISM: Artificial Sequence
<220> FEATURE:
<223> OTHER INFORMATION: Description of Artificial Sequence: Synthetic
      5' F-pc-rh primer

<400> SEQUENCE: 54
atactttaac gtcaaggaga aaaaaccccg gatccatgtg gggtagagac aacaactcc    59

<210> SEQ ID NO 55
<211> LENGTH: 53
<212> TYPE: DNA
<213> ORGANISM: Artificial Sequence
<220> FEATURE:
<223> OTHER INFORMATION: Description of Artificial Sequence: Synthetic
      R2139S1 primer

<400> SEQUENCE: 55
gagctcttaa tccattcctg gctttaattt tactggtaca gtttcaattg gac    53

<210> SEQ ID NO 56
<211> LENGTH: 56
<212> TYPE: DNA
<213> ORGANISM: Artificial Sequence
<220> FEATURE:
<223> OTHER INFORMATION: Description of Artificial Sequence: Synthetic
      sequence for optimum homologous recombination and for the
      expression of the viral protease

<400> SEQUENCE: 56
ggatccctat tgagactgta ccagtaaaat taaagccagg aatggattaa gagctc    56

<210> SEQ ID NO 57
<211> LENGTH: 88
<212> TYPE: DNA
<213> ORGANISM: Artificial Sequence
<220> FEATURE:
<223> OTHER INFORMATION: Description of Artificial Sequence: Synthetic
      modified nucleic acid fragments for optimum homologous
      recombination and for the expression of the viral protease

<400> SEQUENCE: 57
ggatccatgt ggggtagaga caacaactcc ctcgagtcct attgagactg taccagtaaa    60
attaaagcca ggaatggatt aagagctc    88

<210> SEQ ID NO 58
<211> LENGTH: 60
<212> TYPE: DNA

```
<213> ORGANISM: Artificial Sequence
<220> FEATURE:
<223> OTHER INFORMATION: Description of Artificial Sequence: Synthetic
      5' F-pc-rh primer

<400> SEQUENCE: 58
tatactttaa cgtcaaggag aaaaaacccc ggatccatgt ggggtagaga caacaactcc    60

<210> SEQ ID NO 59
<211> LENGTH: 6
<212> TYPE: PRT
<213> ORGANISM: Artificial Sequence
<220> FEATURE:
<223> OTHER INFORMATION: A element
<220> FEATURE:
<221> NAME/KEY: misc_feature
<222> LOCATION: (1)..(1)
<223> OTHER INFORMATION: M or T
<220> FEATURE:
<221> NAME/KEY: misc_feature
<222> LOCATION: (5)..(5)
<223> OTHER INFORMATION: N or S
<220> FEATURE:
<221> NAME/KEY: misc_feature
<222> LOCATION: (6)..(6)
<223> OTHER INFORMATION: F or L

<400> SEQUENCE: 59

Xaa Val Ser Phe Xaa Xaa
1               5
```